United States Patent
Iinuma et al.

(10) Patent No.: US 8,557,864 B2
(45) Date of Patent: Oct. 15, 2013

(54) AGENT HAVING NEUROTROPHIC FACTOR-LIKE ACTIVITY

(75) Inventors: Munekazu Iinuma, Gifu (JP); Shoei Furukawa, Gifu (JP)

(73) Assignees: Nagoya Industrial Science Research Institute, Nagoya-shi (JP); Nippon Zoki Pharmaceutical Co., Ltd., Osaka-shi (JP)

( * ) Notice: Subject to any disclaimer, the term of this patent is extended or adjusted under 35 U.S.C. 154(b) by 0 days.

(21) Appl. No.: 13/439,058

(22) Filed: Apr. 4, 2012

(65) Prior Publication Data

US 2012/0264959 A1  Oct. 18, 2012

Related U.S. Application Data

(62) Division of application No. 12/678,671, filed as application No. PCT/JP2008/066812 on Sep. 18, 2008, now abandoned.

(30) Foreign Application Priority Data

Sep. 19, 2007 (JP) ................. 2007-242563

(51) Int. Cl.
*A61K 31/21* (2006.01)
*C07C 59/147* (2006.01)
*A61P 25/28* (2006.01)

(52) U.S. Cl.
USPC ......... 514/506; 514/17.7; 514/17.8; 514/529; 514/557; 514/558; 554/121; 554/1

(58) Field of Classification Search
None
See application file for complete search history.

(56) References Cited

U.S. PATENT DOCUMENTS

| | | | |
|---|---|---|---|
| 2,496,270 A * | 2/1950 | Coler | 424/10.31 |
| 4,560,785 A | 12/1985 | Honda et al. | |
| 4,665,201 A | 5/1987 | Honda et al. | |
| 6,049,013 A * | 4/2000 | Ueoka et al. | 568/700 |
| 6,201,021 B1 * | 3/2001 | Ohuchida et al. | 514/558 |
| 6,576,660 B1 | 6/2003 | Liao et al. | |
| 6,645,955 B1 | 11/2003 | Liao et al. | |

(Continued)

FOREIGN PATENT DOCUMENTS

| | | | |
|---|---|---|---|
| EP | 1685832 | * | 8/2006 |
| JP | A 58-135878 | | 8/1983 |

(Continued)

OTHER PUBLICATIONS

Nervous disorder, 2003-2012, Prinston University, Farlex, Inc. (abstract); the free dictionary.*

(Continued)

*Primary Examiner* — Yate K Cutliff
(74) *Attorney, Agent, or Firm* — Oliff & Berridge, PLC

(57) ABSTRACT

A method for preventing or treating a nervous disorder can include administrating to a person in need of such prevention or treatment a pharmaceutical preparation comprising, as an active ingredient, an ester of a decenoic acid. The ester of the decenoic acid can be selected from the group consisting of trans-2-decenoic acid ethyl ester, trans-2-decenoic acid methyl ester, trans-2-decenoic acid-2-decenyl ester, trans-2-decenoic acid cyclohexyl ester, trans-2-decenoic acid octyl ester, trans-2-decenoic acid isopropyl ester, trans-3-decenoic acid methyl ester, trans-3-decenoic acid ethyl ester, trans-9-decenoic acid methyl ester, and trans-9-decenoic acid ethyl ester.

10 Claims, 33 Drawing Sheets

(56) References Cited

U.S. PATENT DOCUMENTS

| | | | |
|---|---|---|---|
| 6,652,866 | B1* | 11/2003 | Hertha .................. 424/401 |
| 2002/0107233 | A1 | 8/2002 | Liao et al. |
| 2002/0193357 | A1 | 12/2002 | Song et al. |
| 2003/0105030 | A1 | 6/2003 | Liao et al. |
| 2003/0139385 | A1 | 7/2003 | Song et al. |
| 2003/0144346 | A1 | 7/2003 | Liao et al. |
| 2003/0153541 | A1 | 8/2003 | Dudley et al. |
| 2004/0152681 | A1 | 8/2004 | Liao et al. |
| 2006/0025393 | A1 | 2/2006 | Liao et al. |
| 2007/0197484 | A1 | 8/2007 | Song et al. |
| 2010/0093687 | A1 | 4/2010 | Song et al. |
| 2011/0160174 | A1 | 6/2011 | Song et al. |

FOREIGN PATENT DOCUMENTS

| | | | |
|---|---|---|---|
| JP | A 59-161331 | | 9/1984 |
| JP | A 7-173166 | | 7/1995 |
| JP | A-07-316092 | | 12/1995 |
| JP | A-2000-007568 | | 1/2000 |
| JP | A-2002-080467 | | 3/2002 |
| JP | A-2003-113085 | | 4/2003 |
| JP | A 2003-524577 | | 8/2003 |
| JP | A-2003-261545 | | 9/2003 |
| JP | A-2007-217311 | | 8/2007 |
| WO | WO 01/10447 A1 | | 2/2001 |
| WO | WO 02/068005 | * | 9/2002 |
| WO | WO 03/084542 | | 10/2003 |
| WO | WO 2005/032535 | | 4/2005 |
| WO | WO 2007/068745 A1 | | 6/2007 |

OTHER PUBLICATIONS

Duman et al., "A role for MAP kinase signaling in behavioral models of depression and antidepressant treatment," Biol. Psychiatry 2007; 61:661-670.

Lynch et al., "Brain-derived neurotrophic factor restores synaptic plasticity in a knock-in mouse model of Huntington's Disease," The Journal of Neuroscience 2007; 27(16):4424-4434.

Lang et al., "Association of a functional BDNF polymorphism and anxiety-related personality traits," Psychopharmacology 2005; 180:95-99.

Muller et al., "Brain-derived neurotrophic factor (BDNF) gene and rapid-cycling bipolar disorder," British Journal of Psychiatry 2006; 189:317-323.

Matsushita et al., "Brain-derived neurotrophic factor gene polymorphisms and Alzheimer's disease," J. Neural Transm. 2005; 112:703-711.

Momose et al., "Association studies of multiple candidate genes for Parkinson's disease using single nucleotide polymorphisms" Annals of Neurology, vol. 51, No. 1, pp. 133-136 (2002).

Suleyman Ian, M.A. et al, "The effects of short-chain fatty acids on the neuronal membrane functions of *Helix pomatia*. I. Electrical properties," Cell Mol. Neurobiol, 1986, vol. 6, No. 2, p. 151-163.

Arvanov, V.L. et al., "The effects of short-chain fatty acids on the neuronal membrane functions of *Helix pomatia*. II. Cholinoreceptive properties," Cell Mol. Neurobiol, 1986, vol. 6, No. 2, p. 165-174.

Horie, H. et al., "Cell membrane expansion and blockage of action potentials produced by 2-decenoic acid in cultured dorsal root ganglion neurons," Brain Res, 1987, vol. 411, No. 2, p. 298-303.

Takenaka, T. et al., "Effects of fatty acids on membrane currents in the squid giant axon," J. Membr. Biol, vol. 95, No. 2, p. 113-120.

Sen et al.; "A BDNF Coding Variant Is Associated with the NEO Personality Inventory Domain Neuroticism, a Risk Factor for Depression;" *Neuropsychopharmacology* 28 (2003); pp. 397-401.

Ni et al; "Lead Discovery of a,β-Unsaturated Sulfones from a Combinatorial Library as Inhibitors of Inducible VCAM-1 Expression;" Bioorganic & Medicinal Chemistry Letters; 2003; vol. 13; pp. 745-748.

* cited by examiner

A. BDNF

B. NT-3

C. NGF

D. GR

AGENT HAVING NEUROTROPHIC FACTOR-LIKE ACTIVITY

This is a Divisional of application Ser. No. 12/678,671 filed Mar. 17, 2010, which is a National Stage of Application No. PCT/JP2008/066812 filed Sep. 18, 2008. The prior applications, including the specifications, drawings and abstracts are incorporated herein by reference in their entirety.

TECHNICAL FIELD

The present invention relates to an agent having a neurotrophic factor-like activity, which is useful for nervous disorders such as neurodegenerative diseases and depression due to promotion of activation of nerve cells, by activating signal transmission with a neurotrophic factor-like activity of a nervous growth factor (NGF), a brain-derived neurotrophic factor (BDNF), and the like.

BACKGROUND ART

A nerve cell is a cell having an information transmission function, and its damage emerges as serious loss of a cranial nerve function. Regeneration of an axon can hardly be expected in central nerves of a brain and spinal cord, and thus, when nerve cells have damage or degeneration, activation of the nerve cells is required. A neurotrophic factor is indispensable for activation of nerve cells of central nerves and peripheral nerves such as differentiation of nerve cells, survival sustention, promotion of synapse functions, regeneration and restoration in damage of nerve cells, and the like. Among neurotrophic factors, a nervous growth factor (NGF), a brain-derived neurotrophic factor (BDNF), neurotrophin-3 (NT-3), neurotrophin-4/5 (NT-4/5), and the like construct a neurotrophin family having 50% or more of sequence homology with a nervous growth factor (NGF) as a prototype. Activation of nerve cells is achieved by bonding a neurotrophic factor secreted outside the cells with a high-affinity receptor (Trks) to activate signal transmission through a MAP kinase (mitogen-activated protein (MAP) kinase) information transmission path that activates (phosphorylates) MAP kinases in the nerve cells, and controlling numerous genetic expressions through activation of CREB (c-AMP-response element binding protein) of a transcription factor, and the like.

Therefore, if signal transmission through a MAP kinase information transmission path can be activated, there is a possibility of clinical applications to a nervous disorder caused by degeneration of nerve cells or cellular death. Further, there is a report about a relation between brain-derived neurotrophic factors (BDNF) and some diseases. On the basis of studies using a polymorphism of a brain-derived neurotrophic factor (BDNF), there are a report that a brain-derived neurotrophic factor (BDNF) is associated with Parkinson's disease (see Non-patent Document 1), a report that a brain-derived neurotrophic factor (BDNF) is associated with Alzheimer's disease (see Non-patent Document 2), a report that a brain-derived neurotrophic factor (BDNF) is associated with depression (see Non-patent Document 3), a report that a brain-derived neurotrophic factor (BDNF) is associated with bipolar depression (see Non-patent Document 4), and a report that a brain-derived neurotrophic factor (BDNF) is associated with anxiety disorder (see Non-patent Document 5). Furthermore, there are a report that decrease in a synapse function of a genetically converted mouse having Huntington's disease is cured with administration of a brain-derived neurotrophic factor (BDNF) (see Non-patent Document 6), and a report that administration of a MAP kinase phosphorylation inhibitor provokes an antidepressant condition (see Non-patent Document 7). Accordingly, neurotrophic factors are expected to have an effect as a therapeutic agent for nervous disorders. However, since neurotrophic factors are polymer proteins, they have a problem of having difficulty in reaching the brain since they cannot pass through a blood-brain barrier even if administered from a peripheral. Thus, it has been tried to search medical drugs having a neurotrophic factor-like activity that activates nerve cells with a low-molecular weight compound and medical drugs promoting production and secretion of neurotrophic factors.

Conventionally, an agent having a neurotrophic factor-like activity containing a compound having a predetermined general formula has been proposed (Patent Documents 1 and 2). A production and secretion accelerator of a neurotrophic factor containing a compound having a predetermined general formula (see Patent Documents 3 to 5) and a nerve regeneration accelerator containing fatty acid compounds, salts thereof or prodrugs thereof (see Patent Document 6) have been proposed.

Furthermore, there has been a proposal for a pharmaceutical agent containing a compound having a predetermined general formula, which prevents and cures neurodegenerative diseases with improvement of decrease in GABAA receptor response of an astrocyte (see Patent Document 7).

Non-patent Document 1: Ann Neural. 2002 January; 51(1): 133-6
Non-patent Document 2: J Neural Transm. 2005 May; 112 (5): 703-11. Epub 2004 Sep. 14
Non-patent Document 3: Neuropsychopharmacology. 2003 February; 28(2): 397-401. Epub 2002 Aug. 29
Non-patent Document 4: Br J. Psychiatry. 2006 October; 189: 317-23
Non-patent Document 5: Psychopharmacology (Berl). 2005 June; 180(1): 95-9. Epub 2005 Jan. 26
Non-patent Document 6: J. Neurosci. 2007 Apr. 18; 27(16): 4424-34
Non-patent Document 7: BIOL PSYCHIATRY 2007; 61: 661-670
Patent Document 1: Japanese Unexamined Patent Application (JP-A) No. 2000-7568
Patent Document 2: JP-A No. 2003-113085
Patent Document 3: JP-A No. 2002-80467
Patent Document 4: JP-A No. 2003-261545
Patent Document 5: WO No. 2003/084542
Patent Document 6: WO No. 2005/032535
Patent Document 7: JP-A No. H07-316092

DISCLOSURE OF THE INVENTION

Problems to be Solved by the Invention

The agents having neurotrophic factor-like activities or the production and secretion accelerators of neurotrophic factors described in Patent Documents 1 to 5 do not contain fatty acids or fatty acid esters as active ingredients. In the nerve regeneration accelerator described in Patent Document 6, an active ingredient disclosed with a pharmacological activity of nerve regeneration is (2R)-2-propyloctanoic acid. The pharmaceutical agent for preventing and curing neurodegenerative diseases described in Patent Document 7 contains a saturated fatty acid having 10 or less carbon atoms (C10), an unsaturated fatty acid or saturated fatty acid ester each having 5 carbon atoms (C5) as an active ingredient.

An object of the present invention is to provide a pharmaceutical agent having high safety and a neurotrophic factor-like activity, which contains a predetermined fatty acid or fatty acid ester as an active ingredient.

Means for Solving the Problems

A gist of the present invention lies in an agent having a neurotrophic factor-like activity, containing, as an active ingredient, any one compound included in fatty acids each having 8 carbon atoms (C8) or having 10 carbon atoms (C10) to 12 carbon atoms (C12) or fatty acid esters thereof, such as n-octanoic acid methyl ester, n-octanoic acid ethyl ester, 3,7-dimethyloctanoic acid ethyl ester, or geranic acid ethyl ester, each of which has 8 carbon atoms (C8) decanoic acid methyl ester, decanoic acid ethyl ester, trans-2-decenoic acid, trans-2-decenoic acid methyl ester, trans-2-decenoic acid ethyl ester, trans-2-decenoic acid-2-decenyl ester, trans-2-decenoic acid cyclohexyl ester, trans-2-decenoic acid octyl ester, trans-2-decenoic acid isopropyl ester, trans-3-decenoic acid methyl ester, trans-3-decenoic acid ethyl ester, trans-9-decenoic acid, trans-9-decenoic acid methyl ester, or trans-9-decenoic acid ethyl ester, each of which has 10 carbon atoms (C10), trans-10-undecenoic acid methyl ester, or trans-10-undecenoic acid ethyl ester, each of which has 11 carbon atoms (C11), and dodecanoic acid, dodecanoic acid methyl ester, or dodecanoic acid ethyl ester, each of which has 12 carbon atoms (C12), or salts thereof or prodrugs thereof.

A gist of the present invention lies in the agent having a neurotrophic factor-like activity for a preventive and therapeutic agent for a nervous disorder. The nervous disorder may be a neurodegenerative disease such as Alzheimer's disease, Parkinson's disease, amyotrophic lateral sclerosis (ALS), Huntington's disease, progressive supranuclear palsy (PSP), or diabetic neuropathy. The nervous disorder may be a mental disease, and the mental disease may be depression or anxiety disorder (neurosis).

A gist of the present invention lies in trans-2-decenoic acid-2-decenyl ester, having a neurotrophic factor-like activity. A gist of the present invention lies in trans-2-decenoic acid cyclohexyl ester, having a neurotrophic factor-like activity.

Effect of the Invention

The agent having a neurotrophic factor-like activity of the present invention is useful as a preventive and therapeutic agent for a nervous disorder, which has high safety and activates signal transmission through a MAP kinase information transmission path. The agent is useful as a preventive and improving agent for a neurodegenerative disease such as Alzheimer's disease, Parkinson's disease, amyotrophic lateral sclerosis (ALS), Huntington's disease, progressive supranuclear palsy (PSP), or diabetic neuropathy in nervous disorders. The agent is useful as a preventive and improving agent for a mental disease in the nervous disorder. The agent is useful as a preventive and improving agent for depression or anxiety disorder (neurosis) in the mental disease. In particular, the agent can be expected to have an immediate antidepressant effect and antianxiety effect as a preventive and improving agent for depression or anxiety disorder (neurosis).

BRIEF DESCRIPTION OF DRAWINGS

FIG. 32A is a graph showing ratios of alternation behavior (%) of respective test groups, and FIG. 32B is a graph showing the numbers of total arm selection (total arm entries) of respective test groups.

FIG. 33A is a graph showing time for the mice to explore a "familiar object" and a "novel object" (exploration time), and FIG. 33B is a graph showing recognition indices.

BEST MODE FOR CARRYING OUT THE INVENTION

Figure 1:
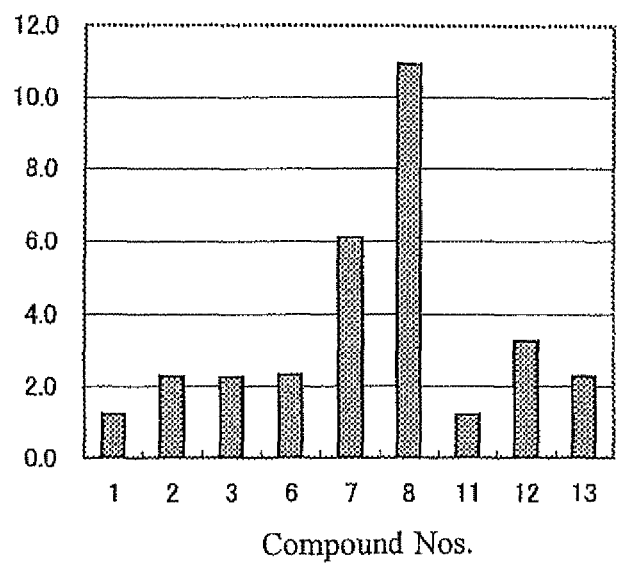
FIG. 1 is a graph showing ratios of phosphorylated MAP kinases to MAP kinases of compounds 1, 2, 3, 6, 7, 8, 11, 12 and 13 in Example 1.

Commercially available products can be used as a fatty acid that is an active ingredient of the agent having a neurotrophic factor-like activity of the present invention, or can be produced in known methods in the same manner as the commercially available products. A fatty acid ester that is an active ingredient of the agent having a neurotrophic factor-like activity of the present invention can be produced in known methods. For examples, it can be produced by the Fischer esterification method in which a fatty acid and an alcohol are reacted in the presence of an acid catalyst, or a transesterification method. Furthermore, it can be produced by substituting a hydroxyl group of a fatty acid to a halogen with a thionyl chloride, sulfuryl chloride, phosphorus trichloride, phosphorus pentachloride, oxalyl chloride, phosphoric trichloride, or the like to give acyl halide and reacting the acyl halide with an alcohol. The produced fatty acid ester can be isolated using known separation and purification techniques such as extraction, partition, and column chromatography, after completion of the reaction.

The fatty acid or the fatty acid ester is any one compound included in fatty acids each having 8 carbon atoms (C8) or having 10 carbon atoms (C10) to 12 carbon atoms (C12) or fatty acid esters thereof, such as n-octanoic acid methyl ester, n-octanoic acid ethyl ester, 3,7-dimethyloctanoic acid ethyl ester, or geranic acid ethyl ester, each of which has 8 carbon atoms (C8), decanoic acid methyl ester, decanoic acid ethyl ester, trans-2-decenoic acid, trans-2-decenoic acid methyl ester, trans-2-decenoic acid ethyl ester, trans-2-decenoic acid-2-decenyl ester, trans-2-decenoic acid cyclohexyl ester, trans-2-decenoic acid octyl ester, trans-2-decenoic acid isopropyl ester, trans-3-decenoic acid methyl ester, trans-3-decenoic acid ethyl ester, trans-9-decenoic acid, trans-9-decenoic acid methyl ester, or trans-9-decenoic acid ethyl ester, each of which has 10 carbon atoms (C10), trans-10-undecenoic acid methyl ester, or trans-10-undecenoic acid ethyl ester, each of which has 11 carbon atoms (C11), and dodecanoic acid, dodecanoic acid methyl ester, or dodecanoic acid ethyl ester, each of which has 12 carbon atoms (C12). One kind or combination of two kinds or more of these compounds can be suitably used.

The fatty acids or fatty acid esters can also be isolated fatty acids or fatty acid esters, or pharmaceutically acceptable salts thereof or prodrugs thereof. Examples of the salts include alkali metal salts such as sodium salt and potassium salt; alkali earth metal salts such as magnesium salt and calcium salt; inorganic acids such as hydrochloric acid, sulfuric acid, phosphoric acid, and hydrobromic acid; alkanol amines such as ammonium salt and triethanol amine; and acid addition salts of organic acids such as acetic acid, formic acid, fumaric acid, and oxalic acid. The fatty acids or fatty acid esters can be solvates of the fatty acids or fatty acid esters. Examples of the solvates include hydrates and alcoholates.

The agent having a neurotrophic factor-like activity is useful for prevention and treatment of nervous disorders. The nervous disorder refers to a clinical condition of damaging functions of nerve cells due to degeneration and cell death of the nerve cells, and includes neurodegenerative diseases and mental diseases. The neurodegenerative diseases refer to Alzheimer's disease, Parkinson's disease, amyotrophic lateral sclerosis (ALS), Huntington's disease, progressive supranuclear palsy (PSP), diabetic neuropathy, etc. The mental diseases refer to depression (including bipolar depression), anxiety disorder (neurosis), integration disorder syndrome, etc. When the agent is used for depression, it takes at least 3 to 4 weeks until there appear effects of conventionally existing depression therapeutic agents such as a tricyclic antidepressant, a tetracyclic antidepressant, a selective serotonin reuptake inhibitor (SSRI), a serotonin noradrenalin reuptake inhibitor (SNRT), and the like, and these agents had to be taken periodically during this term; however, the agent having a neurotrophic factor-like activity of the present invention can be expected to have immediate affectivity as compared to existing medical drugs.

An administration form of the agent having a neurotrophic factor-like activity as a medical drug is not particularly limited, and may be any administration form of oral and parenteral routes. A suitable dosage form can be employed according to an administration form, and the agent can be formed into various preparations such as injectable agents, or oral agents (e.g., capsules, tablets, granules, sprays, pills, subtle granules, etc.), rectal administration agents, oleagenous suppositories, and aqueous suppositories.

Various preparations are prepared by adding vehicles, binding agents, brighteners, disintegrating agents, surfactants, fluidity accelerators, and the like, which are pharmaceutically acceptable and generally used. Examples of the vehicles include lactose, fructose, glucose, cornstarch, sorbit, crystalline cellulose. Examples of the binding agents include methylcellulose, ethyl cellulose, gum arabic, gelatin, hydroxypropyl cellulose, and polyvinyl pyrrolidone. Examples of the brighteners include talc, magnesium stearate, polyethylene glycol, and curing vegetable oils. Examples of the disintegrating agents include starch, sodium alginate, gelatin, calcium carbonate, calcium citrate, dextrin, magnesium carbonate, and synthetic magnesium silicate. Examples of the surfactants include sodium lauryl sulfate, soybean lecithin, sucrose fatty acid esters, and polysorbate 80. Examples of the fluidity accelerators include light anhydrous silicic acid, a dry aluminum hydroxide gel, synthetic aluminum silicate, and magnesium silicate. Examples of other additives include a syrup, vaseline, glycerin, ethanol, propylene glycol, citric acid, sodium chloride, sodium nitrite, and sodium phosphate.

An administration dose of the agent having a neurotrophic factor-like activity can be suitably increased in consideration of a usage, an age, a sex and a degree of a symptom of a patient, and the like, and is generally 1 to 1000 mg, and preferably 5 to 300 mg, per day for an adult, and such a dose can be administered once a day or dividedly administered several times a day.

EXAMPLES

The present invention will be then described in reference to examples, and the present invention is not limited to the following examples.

Production Example 1

Decanoic Acid Methyl Ester, Compound 2

Decanoic acid was dissolved in thionyl chloride (10 ml) and treated in water bath for 3 hours to distill off excess thionyl chloride. Methanol (30 ml) was added to chloride of decanoic acid and refluxed in water bath for 2 hours. After cooling, the reaction mixture was added to 1N HCl (80 ml) to be acidic and distributed with ethyl acetate (hereinafter expressed as "EtOAc"). The distributed liquid was purified with column chromatography (developing solvent: n-hexane ($C_6H_{14}$)-EtOAc (3:1)) after concentration, and decanoic acid methyl ester shown in the following was isolated.

Colorless oily substance, $C_{11}H_{22}O_2$ MW 186, EIMS m/z (%): 186 (M+, 7), 143 (21), 101 (10), 87 (55), 74 (100)

Production Example 2

Decanoic Acid Ethyl Ester, Compound 3

Decanoic acid was dissolved in thionyl chloride (10 ml) and treated in water bath for 3 hours to distill off excess thionyl chloride. Ethanol (30 ml) was added to chloride of decanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and decanoic acid ethyl ester shown in the following was isolated.

Colorless oily substance, $C_{12}H_{24}O_2$ MW 200, EIMS m/z (%): 200 (M+, 10), 155 (26), 101 (44), 88 (100), 73 (19)

Production Example 3

Trans-2-Decenoic Acid Methyl Ester, Compound 7

Trans-2-decenoic acid was dissolved in thionyl chloride (10 ml) and treated in water bath for 3 hours to distill off excess thionyl chloride. Methanol (30 ml) was added to chloride of trans-2-decenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid methyl ester shown in the following was isolated.

Colorless oily substance, $C_{11}H_{20}O_2$ MW 184, EIMS m/z (%): 184 (M+, 5), 167 (6), 153 (43), 123 (16), 113 (41), 87 (90), 69 (39), 43 (100)

Production Example 4

Trans-2-Decenoic Acid Ethyl Ester, Compound 8

Trans-2-decenoic acid was dissolved in thionyl chloride (10 ml) and treated in water bath for 3 hours to distill off excess thionyl chloride. Ethanol (30 ml) was added to chloride of trans-2-decenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid ethyl ester shown in the following was isolated.

Colorless oily substance, $C_{12}H_{22}O_2$ MW 198, EIMS m/z (%): 198 (M+, 9), 171 (27), 153 (56), 110 (11), 91 (100), 71 (44)

Production Example 5

Trans-9-Decenoic Acid Methyl Ester, Compound 12

Trans-9-decenoic acid was dissolved in thionyl chloride (10 ml) and treated in water bath for 3 hours to distill off excess thionyl chloride. Methanol (30 ml) was added to chloride of trans-9-decenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-9-decenoic acid methyl ester shown in the following was isolated.

Colorless oily substance, $C_{11}H_{20}O_2$ MW 184, EIMS m/z (%): 184 (M+, 0), 166 (M+ —$CH_3OH$, 37), 135 (28), 110 (38), 91 (80), 74 (100)

Production Example 6

Trans-9-Decenoic Acid Ethyl Ester, Compound 13

Trans-9-decenoic acid was dissolved in thionyl chloride (10 ml) and treated in water bath for 3 hours to distill off excess thionyl chloride. Ethanol (30 ml) was added to chloride of trans-9-decenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-9-decenoic acid ethyl ester shown in the following was isolated.

Colorless oily substance, $C_{12}H_{22}O_2$ MW 198, EIMS m/z (%): 198 (M+, 0), 152 (M+ —$C_2H_{50}H$, 13), 135 (17), 101 (17), 91 (100)

Production Example 7

Dodecanoic Acid Methyl Ester, Compound 17

Dodecanoic acid was dissolved in thionyl chloride (10 ml) and treated in water bath for 3 hours to distill off excess thionyl chloride. Methanol (30 ml) was added to chloride of dodecanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and dodecanoic acid methyl ester shown in the following was isolated.

Colorless oily substance, $C_{13}H_{26}O_2$ MW 214, EIMS m/z (6): 214 (M+, 13), 185 (15), 171 (15), 143 (17), 87 (64), 74 (100)

Production Example 8

Dodecanoic Acid Ethyl Ester, Compound 18

Dodecanoic acid was dissolved in thionyl chloride (10 ml) and treated in water bath for 3 hours to distill off excess thionyl chloride. Ethanol (30 ml) was added to chloride of dodecanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and dodecanoic acid ethyl ester shown in the following was isolated.

Colorless oily substance, $C_{14}H_{28}O_2$ MW 228, EIMS m/z (%): 228 (M+, 17), 183 (28), 157 (15), 101 (50), 88 (100), 7 (64), 74 (100)

Production Example 9

Trans-10-Undecenoic Acid Methyl Ester, Compound 22

Trans-10-undecenoic acid was dissolved in thionyl chloride (10 ml) and treated in water bath for 3 hours to distill off excess thionyl chloride. Methanol (30 ml) was added to chloride of trans-10-undecenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-10-undecenoic acid methyl ester shown in the following was isolated.

Colorless oily substance, $C_{12}H_{22}O_2$ MW 198, EIMS m/z (%): 198 (M+, 0), 166 (M+ —$CH_3OH$, 22), 149 (13), 124 (36), 87 (53), 74 (100)

Production Example 10

Trans-10-Undecenoic Acid Ethyl Ester, Compound 23

Trans-10-undecenoic acid was dissolved in thionyl chloride (10 ml) and treated in water bath for 3 hours to distill off excess thionyl chloride. Ethanol (30 ml) was added to chloride of trans-10-undecenic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-10-undecenoic acid ethyl ester shown in the following was isolated.

Colorless oily substance, $C_{13}H_{24}O_2$ MW 212, EIMS m/z (%): 212 (M+, 2), 166 (M+ —$CH_3OH$, 32), 149 (20), 124 (38), 101 (44), 88 (84), 69 (34), 41 (100)

Production Example 11 n-octanoic Acid Methyl Ester, Compound 37 n-octanoic acid was dissolved in thionyl chloride (10 ml) and treated in water bath for 3 hours to distill off excess thionyl chloride. Methanol (30 ml) was added to chloride of n-octanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and n-octanoic acid methyl ester shown in the following was isolated.

Colorless oily substance, $C_9H_{19}O_2$ MW 158, EIMS m/z (%): 158 (M+, 4), 127 (27), 115 (11), 88 (43), 74 (100)

Production Example 12 n-octanoic Acid Ethyl Ester, Compound 38 n-octanoic acid was dissolved in thionyl chloride (10 ml) and treated in water bath for 3 hours to distill off excess thionyl chloride. Ethanol (30 ml) was added to chloride of n-octanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and n-octanoic acid ethyl ester shown in the following was isolated.

Colorless oily substance, $C_{10}H_{20}O_2$ MW 172, EIMS m/z (%): 172 (M+, 6), 127 (42), 115 (11), 101 (39), 88 (100)

Production Example 13

Trans-2-Decenoic Acid-Trans-2-Decenyl Ester, Compound 47

Trans-2-decenoic acid was dissolved in thionyl chloride (10 ml) and treated in water bath for 3 hours to distill off excess thionyl chloride. Trans-2-decen-1-ol (30 ml) was added to chloride of trans-2-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid-trans-2-decenyl ester shown in the following was isolated.

Colorless oily substance, $C_{20}H_{36}O_2$ MW 308, EIMS m/z (%): 308 (M+, 8), 153 (100), 138 (12), 110 (10), 91 (36), 69 (24), 55 (35)

Production Example 14

Trans-2-Decenoic Acid Cyclohexyl Ester, Compound 48

Trans-2-decenoic acid was dissolved in thionyl chloride (10 ml) and treated in water bath for 3 hours to distill off excess thionyl chloride. Cyclohexanol (30 ml) was added to chloride of trans-2-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid cyclohexyl ester shown in the following was isolated.

Colorless oily substance, $C_{16}H_{28}O_2$ MW 252, EIMS m/z (%): 252 (M+, 0), 171 (100), 153 (30), 82 (16), 67 (10), 55 (13)

Production Example 15

Trans-2-Decenoic Acid Octyl Ester, Compound 53

Trans-2-decenoic acid was dissolved in thionyl chloride (10 ml) and treated in water bath for 3 hours to distill off excess thionyl chloride 1-octanol (30 ml) was added to chloride of trans-2-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid octyl ester shown in the following was isolated.

Colorless oily substance, $C_{18}H_{34}O_2$ MW 282, EIMS m/z (%): 282 (M+, 1.6), 171 (100), 153 (18), 112 (14), 83 (25), 69 (22), 57 (26)

Production Example 16

Trans-2-Decenoic Acid Isopropyl Ester, Compound 54

Trans-2-decenoic acid was dissolved in thionyl chloride (10 ml) and treated in water bath for 3 hours to distill off excess thionyl chloride. An isopropyl alcohol (30 ml) was added to chloride of trans-2-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-2-decenoic acid isopropyl ester shown in the following was isolated.

Colorless oily substance, $C_{13}H_{24}O_2$ MW 212, EIMS m/z (%): 212 (M+, 1.6), 171 (38), 153 (54), 110 (11), 99 (11), 57 (26), 43 (100)

Production Example 17

Trans-3-Decenoic Acid Methyl Ester, Compound 62

Trans-3-decenoic acid (Wako Pure Chemical Industries, Ltd.) was dissolved in thionyl chloride (10 ml) and treated in water bath for 3 hours to distill off excess thionyl chloride. Methanol (30 ml) was added to chloride of trans-3-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-3-decenoic acid methyl ester shown in the following was isolated.

Colorless oily substance, $C_{11}H_{20}O_2$ MW 184, EIMS m/z (%): 183 (MA-1, 14), 171 (30), 151 (8), 139 (25), 123 (46), 97 (25), 87 (62), 55 (47), 41 (100)

Production Example 18

Trans-3-Decenoic Acid Ethyl Ester, Compound 63

Trans-3-decenoic acid (Wako Pure Chemical Industries, Ltd.) was dissolved in thionyl chloride (10 ml) and treated in water bath for 3 hours to distill off excess thionyl chloride. Ethanol (30 ml) was added to chloride of trans-3-decenoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and trans-3-decenoic acid ethyl ester shown in the following was isolated.

Colorless oily substance, $C_{12}H_{22}O_2$ MW 198, EIMS m/z (%): 197 (M+−1, 23), 185 (31), 157 (20), 139 (52), 123 (100), 101 (85), 73 (56)

Production Example 19

Geranic Acid Ethyl Ester, Compound 77

Geranic acid (Wako Pure Chemical Industries, Ltd.) was dissolved in thionyl chloride (10 ml) and treated in water bath for 3 hours to distill off excess thionyl chloride. Ethanol (30 ml) was added to chloride of geranic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and geranic acid ethyl ester shown in the following was isolated.

Colorless oily substance, $C_{12}H_{20}O_2$ MW 196, EIMS m/z (%): 195 (M+−1, 17), 181 (10), 151 (15), 121 (74), 107 (100), 79 (40), 69 (30)

Production Example 20

3,7-dimethyloctanoic Acid Ethyl Ester, Compound 78

3,7-dimethyloctanoic acid was dissolved in thionyl chloride (10 ml) and treated in water bath for 3 hours to distill off excess thionyl chloride. Ethanol (30 ml) was added to chloride of 3,7-dimethyloctanoic acid and refluxed in water bath for 2 hours. After cooling, the reaction mixture was added to 1N HCl (80 ml) to be acidic and distributed with EtOAc. The distributed liquid was purified with column chromatography (developing solvent: $C_6H_{14}$-EtOAc (3:1)) after concentration, and the 3,7-dimethyloctanoic acid ethyl ester shown in the following was isolated. 3,7-dimethyloctanoic acid was obtained by contact reduction of geranic acid.

Colorless oily substance, $C_{12}H_{24}O_2$ MW 200, EIMS m/z (%): 200 (M+, 6), 198 (10), 185 (6), 153 (22), 128 (24), 115 (68), (100), 69 (45)

Example 1

Measurement of Activation of Map Kinases

Activation of MAP kinases was measured on respective compounds in Table 1 including the compound obtained in Production Example with western immunoblotting as follows. Nerve cells were dispersed from a cerebral cortex of a 17-day-old fetal rat and the nerve cells were cultured in a Dulbecco's modified eagle medium (DMEM) containing 5%; fetal bovine serum for 1 day. A culture solution was exchanged to a serum-free medium (B27 supplement added Neurobasal, Invitrogen Corporation), and the nerve cells were cultured in a culture petri dish coated with polyornithine at a density of 20,000 to 40,000 cells/cm². Three days later, each of the compounds in Table 1 was added thereto, and culture for 30 minutes was continued. Then, cells were recovered on ice with a solution of a Tris-HCL buffer as a base containing a phosphatase inhibitor. The protein concentration of the obtained cell extraction was determined using a BCA Protein Assay Kit (TAKARABIO INC.), a constant amount (3 μg for MAP kinase measurement, 5 μg for phosphorylated MAP kinase measurement) of the protein was electrophoresed with a polyacrylic amide gel. The protein was transcribed to a PVDF membrane from the gel after electrophoresis, and western immunoblotting was carried out using the primary antibodies: an anti-MAP kinase antibody (Cell Signaling Technology, Inc.) and an antiphosphorylated MAP kinase antibody (Cell Signaling Technology, Inc.), respectively. Subsequently, an enzyme activity was subjected to color development by being reacted with the secondary antibody: an alkaline phosphatase labeled anti-rabbit IgG antibody (Promega KK) to measure MAP kinases and phosphorylated MAP kinases. In addition, each compound was dissolved in 0.7% DMSO and adjusted to have a concentration of 500 μg/ml. A control was added with a phosphoric acid buffer containing 0.1% DMSO in the same amount as the compound.

The above obtained concentration measurement of the electrophoresis gel band was digitalized by calculating an intensity with Image J (BioArts International, Inc.). The numerical value of MAP kinases of each compound was divided by the numerical value of the control's MAP kinases, and the numerical value of phosphorylated MAP kinases of each compound was divided by the numerical value of the control's phosphorylated MAP kinases to find a ratio of the MAP kinases of each compound to the control and a ratio of the phosphorylated MAP kinases of the each compound to the control. Then, the obtained ratio of the phosphorylated MAP kinases to the control was divided by the obtained ratio of the MAP kinases to the control to find a ratio of the phosphorylated MAP kinases to the MAP kinases and graphs were formed and shown in FIGS. 1 to 3. Compound 1, compound 6, compound 11, compound 16, compound 21 and compound 36 in Table 1 were used from products made by Wako Pure Chemical Industries, Ltd.

TABLE 1

| Compound Nos. | Compound |
|---|---|
| 1 | decanoic acid |
| 2 | decanoic acid methyl ester |
| 3 | decanoic acid ethyl ester |
| 6 | trans-2-decenoic acid |
| 7 | trans-2-decenoic acid methyl ester |
| 8 | trans-2-decenoic acid ethlyl ester |
| 11 | trans-9-decenoic acid |
| 12 | trans-9-decenoic acid methyl ester |
| 13 | trans-9-decenoic acid ethyl ester |
| 16 | dodecanoic acid |
| 17 | dodecanoic acid methyl ester |
| 18 | dodecanoic acid ethyl ester |
| 21 | trans-10-undecenoic acid |
| 22 | trans-10-undecenoic acid methyl ester |
| 23 | trans-10-undecenoic acid ethyl ester |
| 36 | n-octanoic acid |
| 37 | n-octanoic acid methyl ester |
| 38 | n-octanoic acid ethyl ester |
| 47 | trans-2-decenoic acid-trans-2-decenyl ester |
| 48 | trans-2-decenoic acid cyclohexyl ester |
| 53 | trans-2-decenoic acid octyl ester |
| 54 | trans-2-decenoic acid isopropyl ester |
| 62 | trans-3-decenoic acid methyl ester |
| 63 | trans-3-decenoic acid ethyl ester |
| 77 | geranic acid ethyl ester |
| 78 | 3,7-dimethyloctanoic acid ethyl ester |

Figure 2:
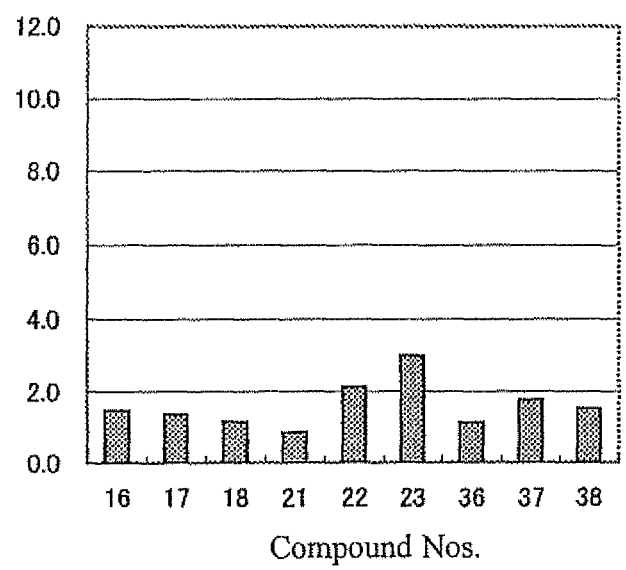
FIG. 2 is a graph showing ratios of phosphorylated MAP kinases to MAP kinases of compounds 16, 17, 18, 21, 22, 23, 36, 37 and 38 in Example 1.
Figure 3:
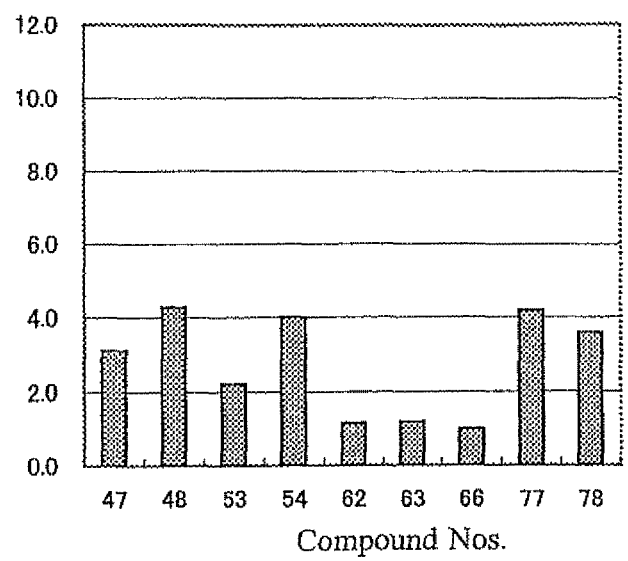
FIG. 3 is a graph showing ratios of phosphorylated MAP kinases to MAP kinases of compounds 47, 48, 53, 54, 62, 63, 77 and 78 in Example 1.

From FIGS. 1 to 3, the compounds shown in Table 1 showed numerical values of one or more times (except for compound 21), and MAP kinases were activated (phosphorylated). In particular, trans-2-decenoic acid esters such as any of the compounds having different alkoxy groups (compound Nos. 7, 8, 47, 48, 53 and 54) showed twice or more numerical values, and high MAP kinase activation (phosphorylation) effects were shown. In particular, trans-2-decenic acid ethyl ester was as high as 11 times, and secondarily, trans-2-decenic acid methyl ester was 6 times. Also, decanoic acid methyl ester, decanoic acid ethyl ester, trans-2-decenoic acid, trans-9-decenoic acid methyl ester, trans-9-decenoic acid ethyl ester, trans-10-undecenoic acid methyl ester, trans-10-undecenoic acid ethyl ester, geranic acid ethyl ester and 3,7-dimethyloctanoic acid ethyl ester showed high activities.

Example 2

Behavior Test of Mice Under Stress (1) Stress

Mice under established chronic mild stress (hereinafter referred to as "stress") were used for a depression and anxiety disorder-like model animal. Stress was applied as follows. 7-week-old male ddY strain mice fed in one cage for 4 mice were used and first subjected to forced swimming for 15 minutes. Then, the mice were fed in a sloped cage for 2 days, and then rested in a normal cage for 1 day. Then, the mice were fed in a dirt cage moisturized with 200 mL of water for 1 day and then rested in a normal cage for 1 day. Then, the mice were fed in a rotational cage that rotated at 180 rpm for 1 day, and then rested in a normal cage for 1 day. Stress taking for 1 week using these 3 kinds of cages was regarded as 1 cycle, and the stress was applied for 3 cycles (3 weeks). At the same time as stress, the compound 8 that was dissolved in 0.1% DMSO to adjust a concentration so as to have each of the doses of 0, 20, 100 and 500 µg/kg was intraperitoneally injected for 3 weeks in an amount of 0.25 mL in each time once per day. The compound 8 was also administered to non-stressed examples for 3 weeks in the same manner. For 0 µg/kg administration examples of controls, a phosphoric acid buffer containing 0.1% DMSO (controls were expressed as "PBS" or "0 µg/kg" in the figure shown below) was administered in an amount of 0.25 mL to each of a stressed example and a non-stressed example. The behavior test of mice was performed on each of the following: an administration group to which the compound 8 was administered at the same time as stress for 3 weeks and an administration group to which the compound 8 was administered for 3 weeks without stress (hereinafter referred to as the "stressed 3 week-administration groups"); and an administration group to which the compound 8 was administered at the same time as stress for 1 week and an administration group to which the compound 8 was administered for 1 week without stress (hereinafter referred to as the "stressed 1 week-administration groups"). Additionally, an example in which stress was applied to a mouse may be referred to as a stressed example, and an example in which stress was not applied to a mouse may be referred to as anon-stressed example Further, a significance test was performed on the results of Examples 1 to 7 in a Student's t-test.

(2) Behavior Test

1. Burying the Glass-Marbles Test

Tips were bedded so as to have a height of 5 cm in a box with 30 m² and 25 glass marbles (1.6 cm in diameter) were placed thereon at 5 cm-interval and behaviors of mice were observed. The number of buried glass marbles was found by counting each glass marble that was buried in ⅔ or more from visual observation from just above after 15 minutes as one count. The test was performed for 3 hours. Since a mouse under stress having an anxiety symptom (condition) takes such a behavior as burying glass marbles, a level of the anxiety symptom can be evaluated from the number of buried glass marbles.

Figure 4:
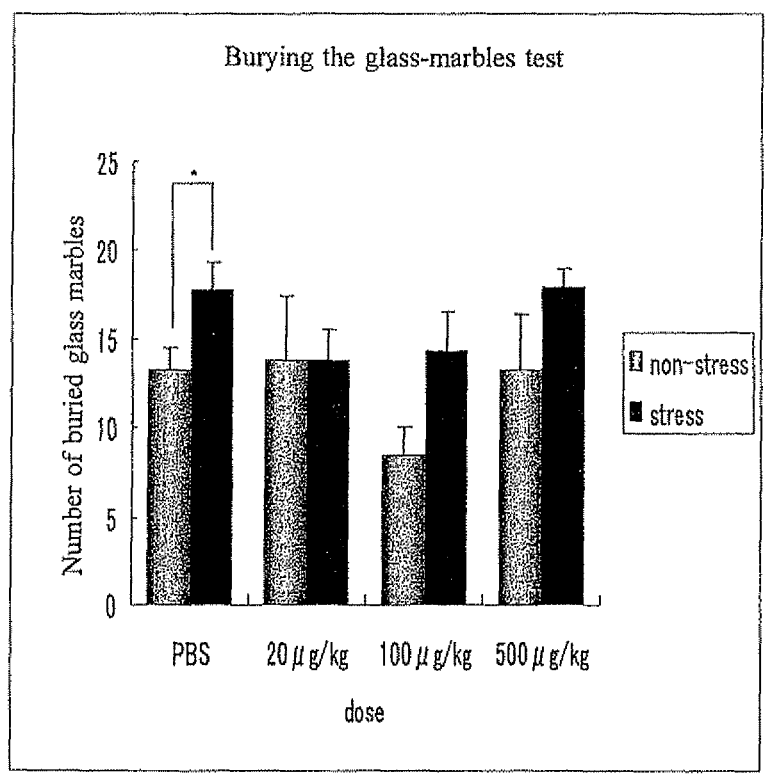
FIG. 4 is a graph of a burying the glass-marbles test of comparing the numbers of buried glass marbles between stressed examples and non-stressed examples of the "stressed 3 week-administration groups" in Example 2.
Figure 5:
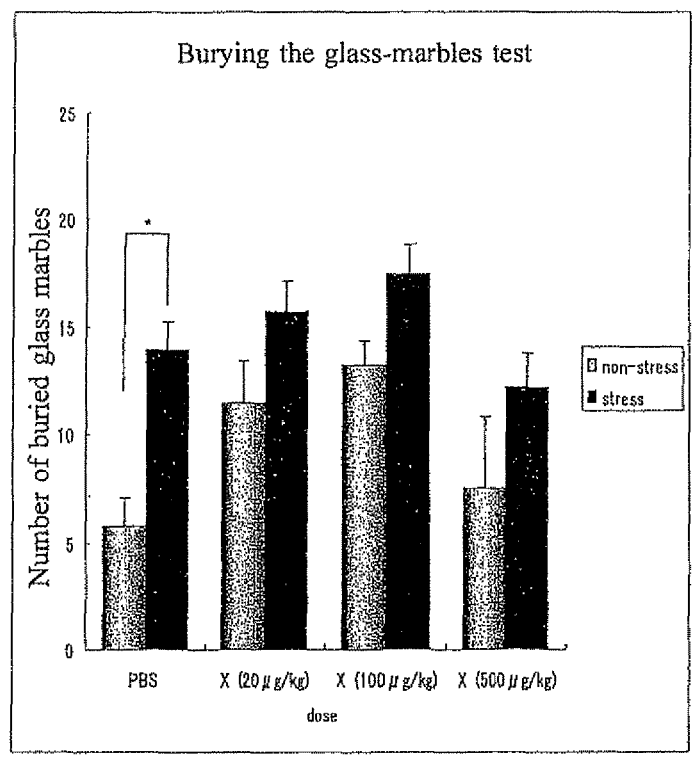
FIG. 5 is a graph of a burying the glass-marbles test of comparing the numbers of burying glass marbles between stressed examples and non-stressed examples of the "stressed 1 week-administration groups" in Example 2.

FIGS. 4 and 5 show the results.

The numbers of glass marbles buried by mice had a significant difference between a stressed example and a non-stressed example of controls (PBS) in any of "the stressed 3 week-administration group" and "the stressed 1 week-administration group"; on the contrary, there was no significant difference between a stressed example and a non-stressed example in each administration example of the administration groups of the compound 8 (see FIGS. 4 and 5), and the compound 8 suppressed an anxiety symptom. From the result of "the stressed 1 week-administration group", the compound 8 is considered to immediately act on the anxiety symptom.

2. Tail Suspension Test

Figure 6:
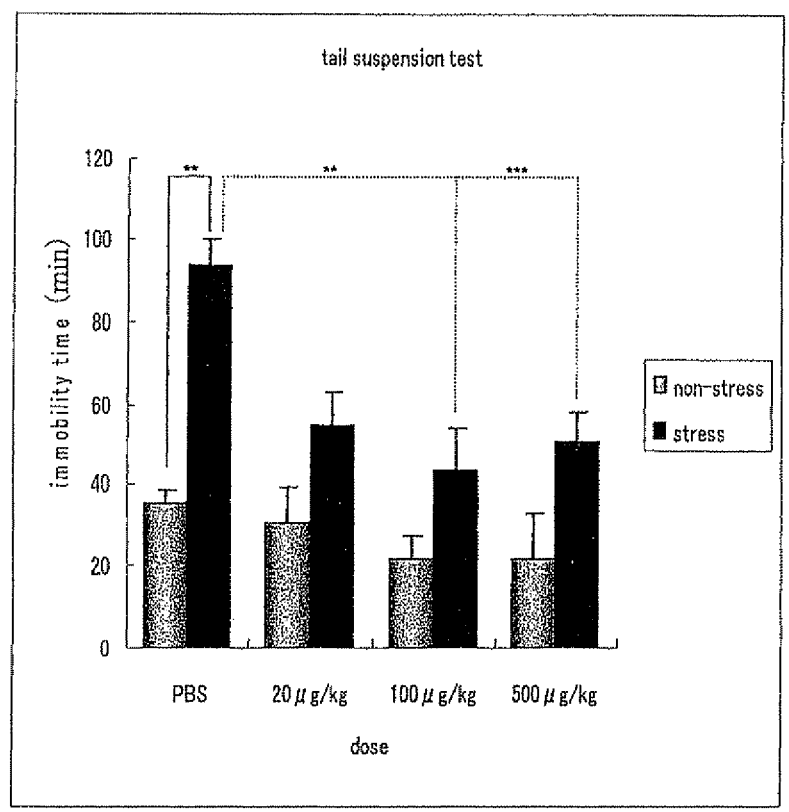
FIG. 6 is a graph of a tail suspension test of comparing immobility times between stressed examples and non-stressed examples of the "stressed 3 week-administration groups" in Example 2.
Figure 7:
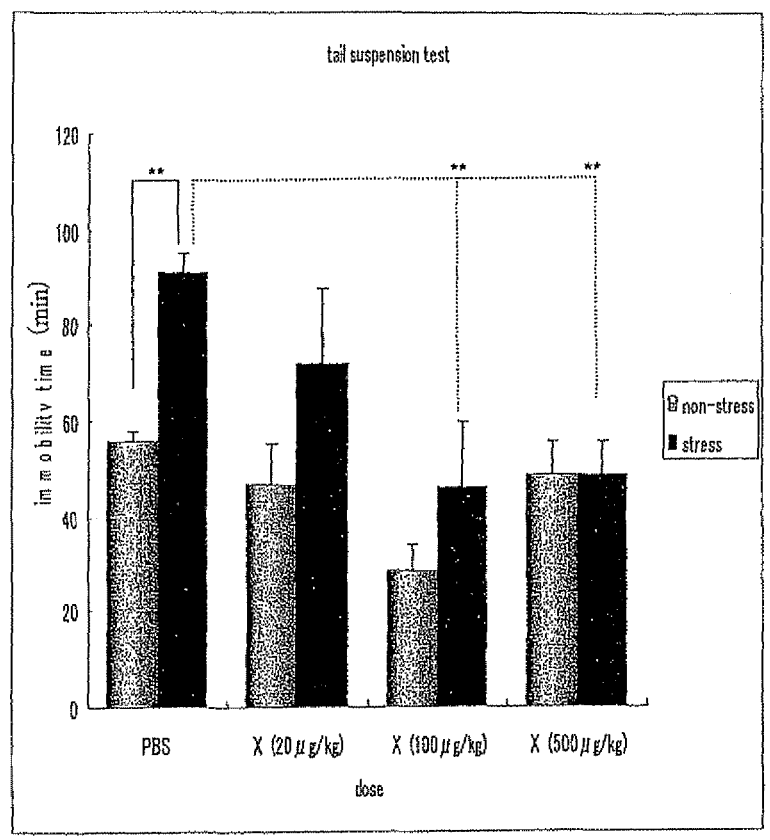
FIG. 7 is a graph of a tail suspension test of comparing immobility times between stressed examples and non-stressed examples of the "stressed 1 week-administration groups" in Example 2.
Figure 8:
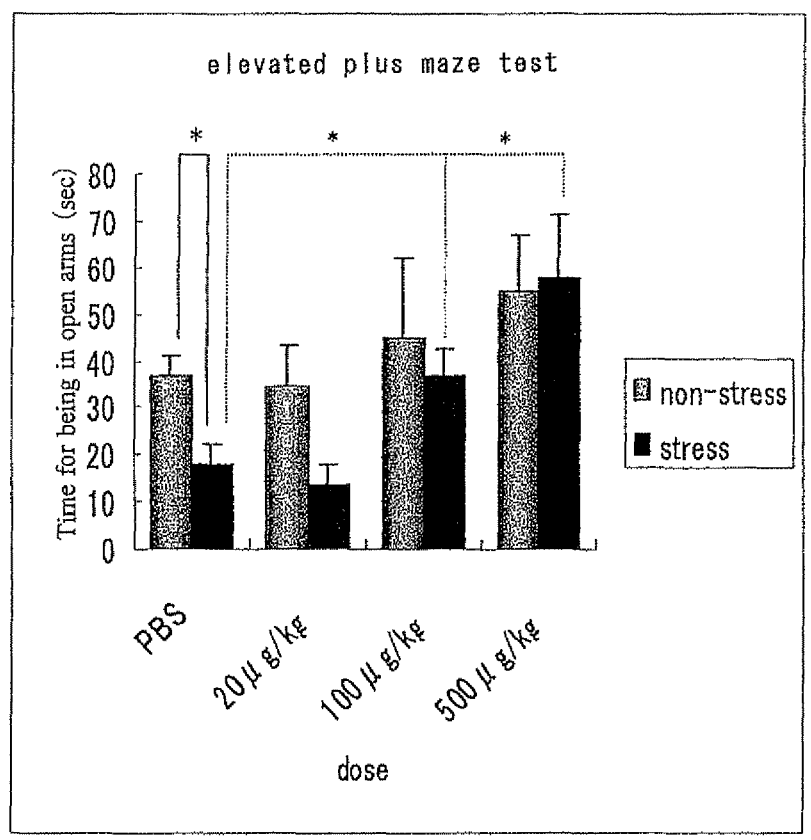
FIG. 8 is a graph of an elevated plus maze test of comparing times for being in open arms between stressed examples and non-stressed examples of the "stressed 3 week-administration groups" in Example 2.
Figure 9:
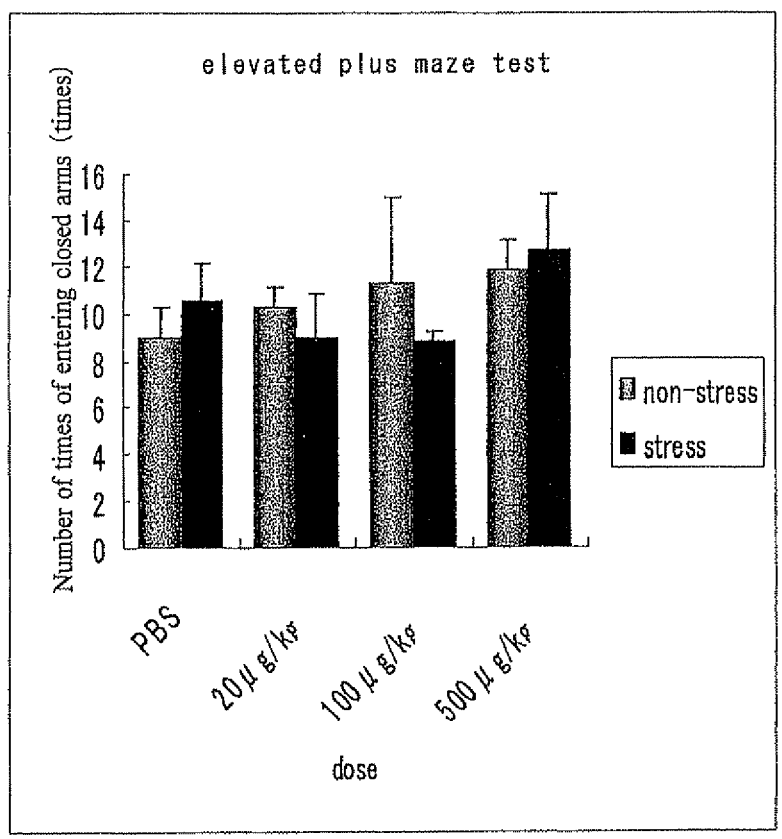
FIG. 9 is a graph of an elevated plus maze test of comparing the numbers of times of entering closed arms between stressed examples and non-stressed examples of the "stressed 3 week-administration groups" in Example 2.
Figure 10:
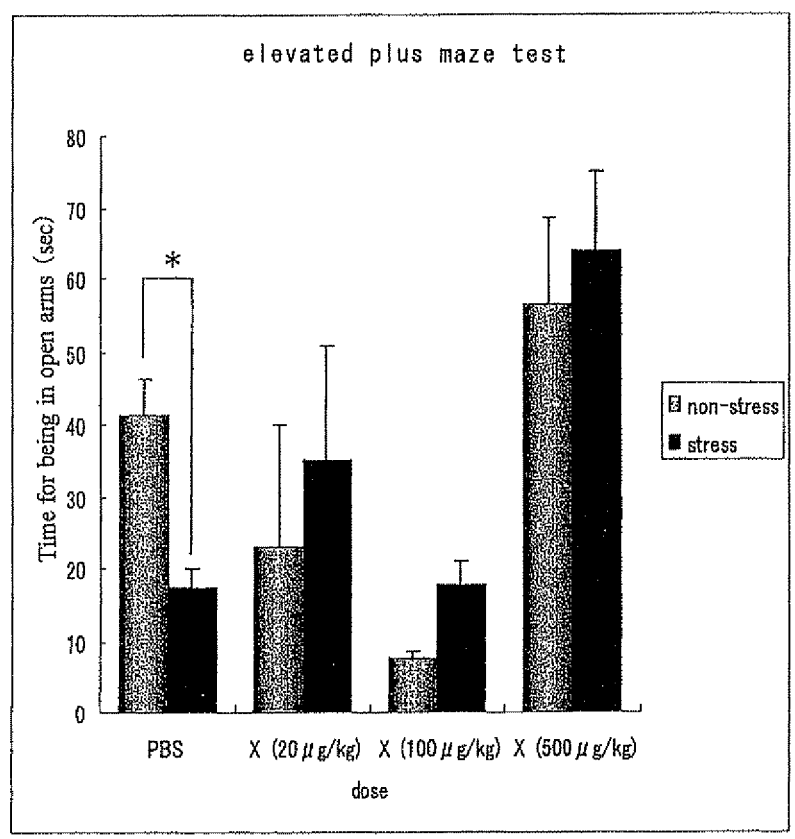
FIG. 10 is a graph of an elevated plus maze test of comparing times for being in open arms between stressed examples and non-stressed examples of the "stressed 1 week-administration groups" in Example 2.
Figure 11:
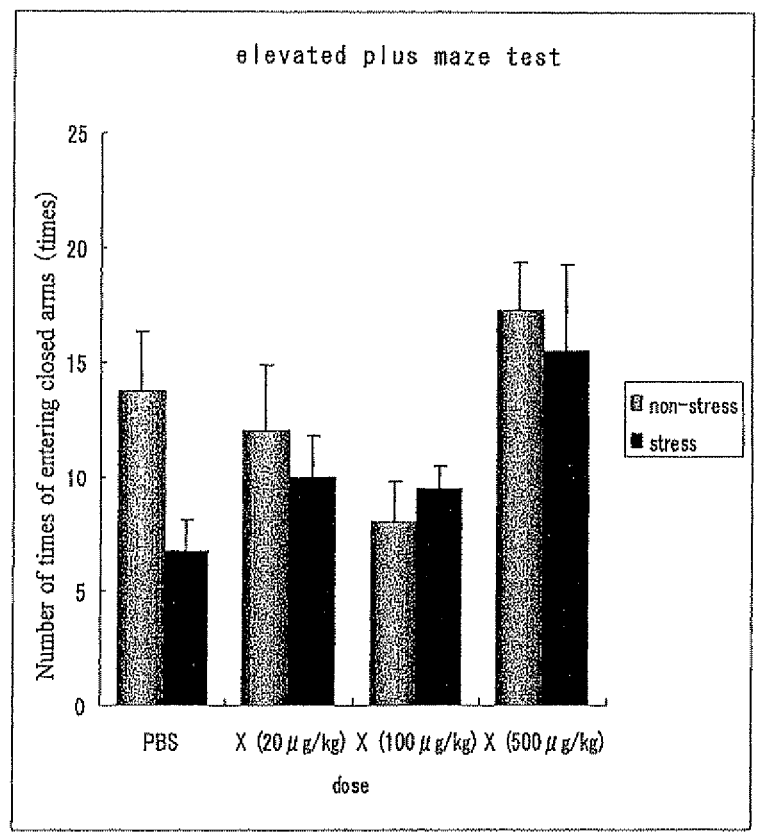
FIG. 11 is a graph of an elevated plus maze test of comparing the numbers of times of entering closed arms between stressed examples and non-stressed examples of the "stressed 1 week-administration groups" in Example 2.

A site of 1 cm from the tip of the tail of a mouse was grasped by a hand, being apart from a floor from 10 cm, and an immobility time in suspension for 6 minutes was measured for 2 hours. Since the immobility time prolongs when the mouse has a depressive symptom (condition), a level of the depressive symptom (condition) can be evaluated from the length of the immobility time. FIGS. 6 and 7 show the results.

The immobility times of mice had a significant difference between a stressed example and a non-stressed example of controls (PBS) in any of "the stressed 3 week-administration groups" and "the stressed 1 week-administration groups"; on the contrary, there was no significant difference between a stressed example and a non-stressed example in each administration example of the administration groups of the compound 8 (see FIGS. 6 and 7), and the compound 8 suppressed a depressive symptom. From the result of "the stressed 1 week-administration group", the compound 8 is considered to immediately act on the depressive symptom.

3. Elevated Plus Maze Test

Using a device having an elevated maze cruciately crossed, in which 10 cm-wall was provided in the X axis (closed arm, 30 cm×10 cm) and no wall was provided in the Y axis (open arm, 30 cm×10 cm), being apart from 50 cm from a floor, behaviors of mice in 5 minutes were observed to measure a time for being in the open arm and the number of times of entering the closed arm. In this test, an anxiety level can be evaluated from the time for being the open arm, and a behavior amount can be evaluated from the number of times of entering the closed arm. From the evaluations, when a mouse has an anxiety symptom (condition), the time for being in the open arm prolongs, and thus, a level of the anxiety symptom (condition) can be evaluated from the length of the time. FIGS. 8 to 11 show the results.

Since the numbers of times when mice entered the closed arm had no significant difference between the control (PBS) and the compound 8 administration groups and between the stressed groups and the non-stressed groups (see FIGS. 9 and 11), administration of the compound 8 did not give an effect on behavior amounts of the mice, and thus, the times when the mice were in the open arm did not depend on the behavior amounts. The times when the mice were in the open arm had a significant difference between stressed examples and non-stressed examples of controls (PBS) in any of "the stressed 3 week-administration groups" and "the stressed 1 week-administration groups", and there was no significant difference between stressed examples and non-stressed examples of each administration example in the compound 8 administration groups (see FIGS. 8 and 10), and the compound 8 thus suppressed the anxiety symptom of mice. From the result of "the stressed 1 week-administration group", the compound 8 is considered to immediately act on the anxiety symptom.

Example 3

Measurement of Weights of Mice Before and after Stress

Figure 12:
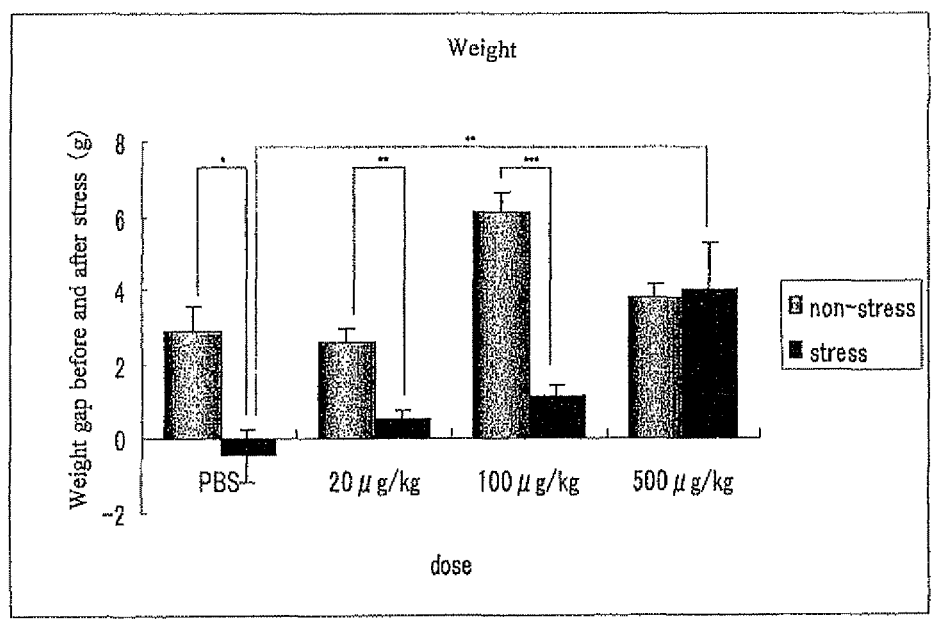
FIG. 12 is a graph comparing gaps of body weights between stressed examples obtained by administering the compound 8 and applying stress for 3 weeks and non-stressed examples in Example 3.

A weight of a mouse before stress was subtracted from the weight of the mouse immediately after administering the compound 8 as well as stress for 3 weeks to obtain a weight gap (g). FIG. 12 shows the result.

FIG. 12 reveals that a weight of a non-stressed example of the control (PBS) increased, and on the other hand, a weight of a stressed example significantly decreased due to depressive and anxiety symptoms. On the other hand, ratios of the weight decreases in stressed examples of the compound 8 administration groups were less due to a suppression effect of the compound 8 on depressive and anxiety symptoms as compared to the control (PBS), and there was no significant difference between a stressed example and a non-stressed example in the 500 µg/kg administration group and an effect on the body weights was not recognized.

Example 4

Measurement of Activation of Map Kinase with Compound 8

After 24 hours from completion of stress for 3 weeks in the same method as described in Example 2, mice administered with the compound 8 in doses of 0, 20, 100 and 500 µg/kg respectively at the same time as stress and non-stressed mice administered with only a phosphoric acid buffer containing 0.1% DMSO were sacrificed and the cortexes of frontal lobes and hippocampi were excised respectively, and thereto were added RIPA buffers in 19 times of an amount of each wet weight.

Figure 13:
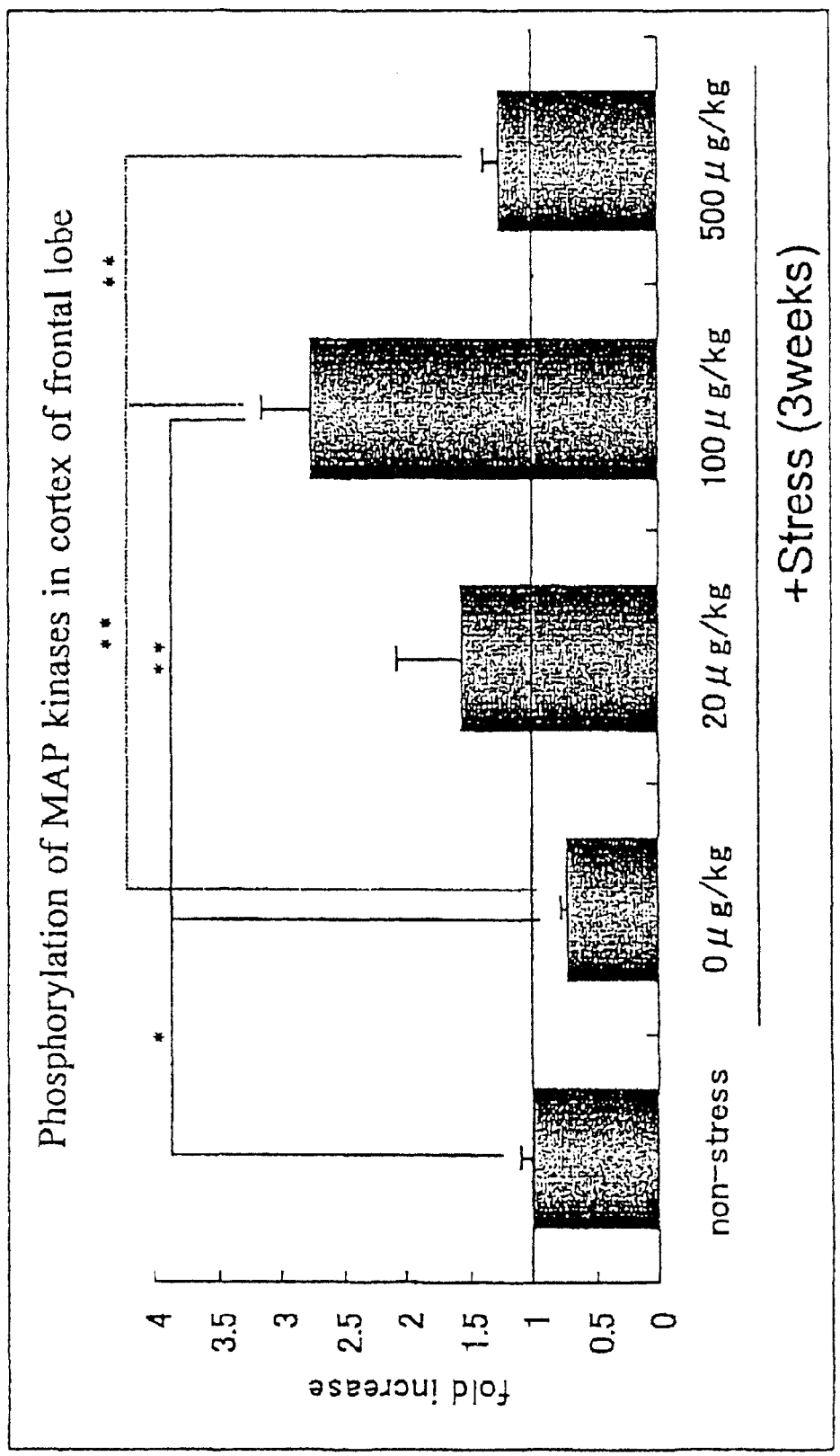
FIG. 13 is a graph comparing phosphorylated MAP kinase amounts in cortexes of frontal lobes between stressed examples obtained by administering the compound 8 and applying stress for 3 weeks and non-stressed examples in Example 4.
Figure 14:
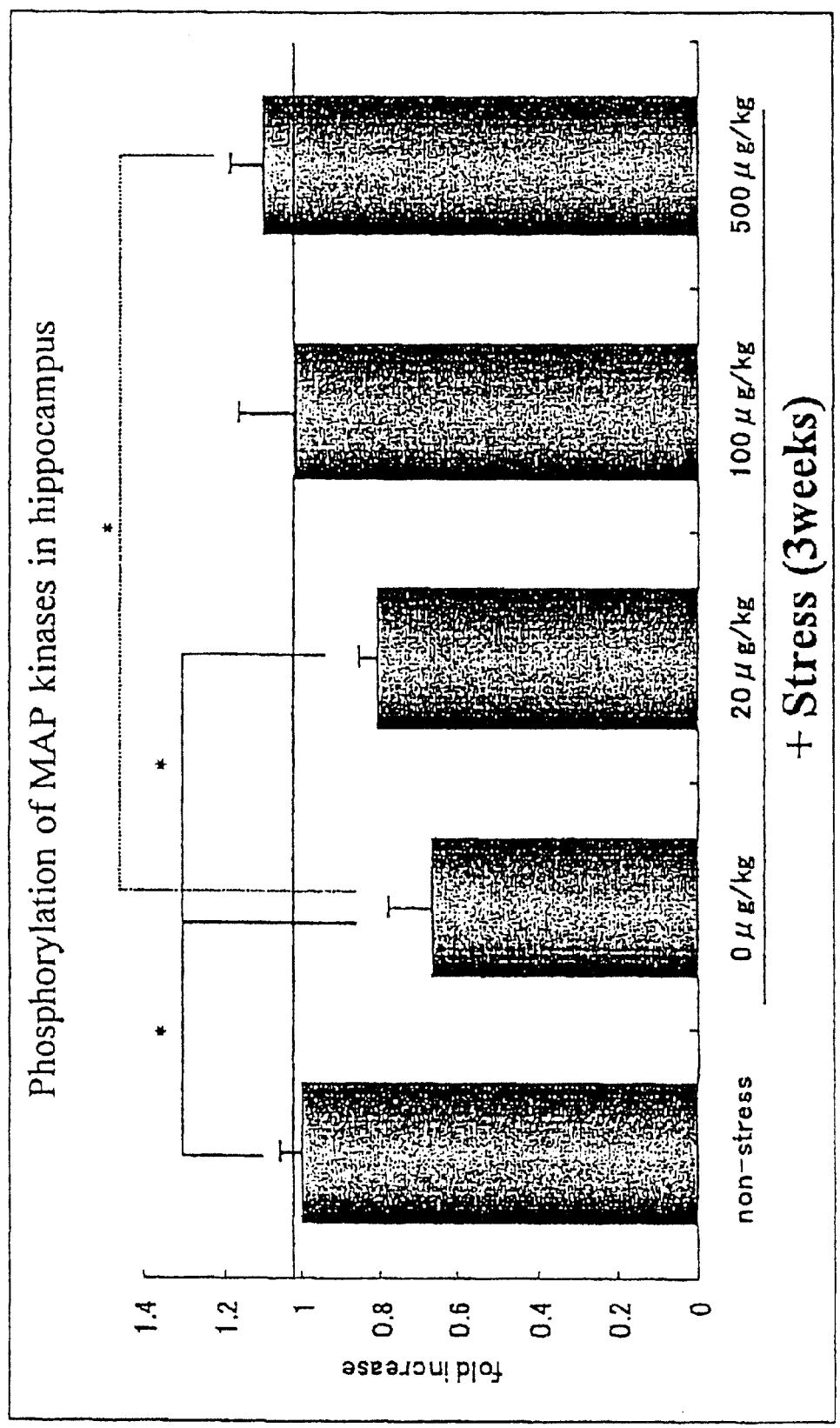
FIG. 14 is a graph comparing phosphorylated MAP kinase amounts in hippocampi between stressed examples obtained by administering the compound 8 and applying stress for 3 weeks and non-stressed examples in Example 4.

Then, sonication was performed by an ultrasonic grinder until tissues cannot be seen, centrifuged at 12000 rpm for 15 minutes, and the supernatant was recovered to form a tissue protein extraction solution. The protein concentration of the extraction solution was measured using a BCA Protein Assay Kit (TAKARA BIO INC.), each of extraction solutions containing 3 µg for a MAP kinase and 5 µg for a phosphorylated MAP kinase was added with a ⅓ amount of a sample buffer for electrophoresis at 4 times of a concentration, and a ¹⁄₁₀ amount of 2-mercaptoethanol and thermally treated at 95° C. for 5 minutes and subjected to electrophoresis with a 10% SDS polyacrylic amide gel. Proteins were then transcribed to a PVDF membrane from the gel and the membrane after transcription was immersed in a block liquid (TBS containing 5% skimmed milk) for 1 hour, and reacted with primary antibodies: an anti-MAP kinase antibody (Cell Signaling Technology, Inc.) and an antiphosphorylated MAP kinase antibody (Cell Signaling Technology, Inc.) overnight, and further reacted with the secondary antibody: an alkaline phosphatase labeled anti-rabbit IgG antibody (Promega KK) for 1 hour. Lastly, a D1G3 buffer was used as the substrate of an alkaline phosphatase and incubated with a liquid obtained by adding nitroblue tetrazolium (NET) and 5-bromo-4-chloro-3-indolylphosphate p-toluidine salt (BCIP) for several minutes to develop a color. For a concentration measurement of a band, an intensity was calculated with Image J (BioArts International, Inc.) to find a phosphorylated MAP kinase amount of each of the compound 8 administration groups to a phosphorylated MAP kinase amount in a non-stressed example. FIGS. 13 and 14 show the results.

FIGS. 13 and 14 reveal that the phosphorylated MAP kinase amount of the control (0 µg/kg) significantly decreased in both of the cortex of frontal lobe and hippocampus as compared to a non-stressed example. On the other hand, the compound 8 administration groups had an administration example in which the phosphorylated MAP kinase amount significantly increased as compared to the control (0 µg/kg) and the compound 8 promoted activation (phosphorylation) of the MAP kinase.

Example 5 mRNA Expression of Neurotrophic Factor and Glucocorticoid Receptor in Cortex of Frontal Lobe and Hippocampus of Mouse mRNA expressions of a brain-derived neurotrophic factor (hereinafter expressed as "BDNF"), neurotrophin-3 (hereinafter expressed as "NT-3"), a nervous growth factor (hereinafter expressed as "NGF") and a glucocorticoid receptor (hereinafter expressed as "GR") in a cortex of frontal lobe and a hippocampus of a mouse after stress were examined as follows. After 24 hours from completion of stress for 3 weeks in the same method as described in Example 2, mice administered with the compound 8 in each of the amounts of 0, 20, 100 and 500 µg/kg, at the same time as stress, and non-stressed mice administered with only a phosphoric acid buffer containing 0.1% DMSO were sacrificed and the cortexes of frontal lobes and hippocampi were excised respectively, and thereto were added TriZol. The both tissues were crashed with a homogenizer respectively, chloroform was then added thereto, and the mixture was centrifuged at 15000 rpm for 15 minutes to take out the aqueous phase. This aqueous phase was added with isopropanol and centrifuged at 15000 rpm for 15 minutes.

Figure 15:
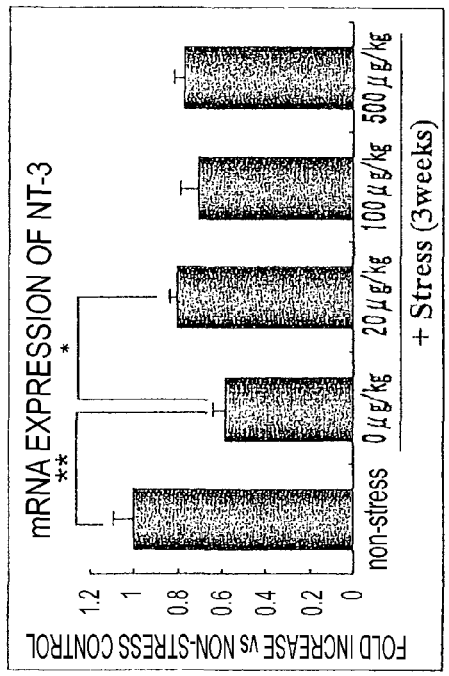
FIG. 15 is a graph comparing expression amounts of mRNAs of BDNF, NT-3, NGF and GR in cortexes of the frontal lobes between stressed examples obtained by administering the compound 8 and applying stress for 3 weeks and non-stressed examples in Example 5.
Figure 15:
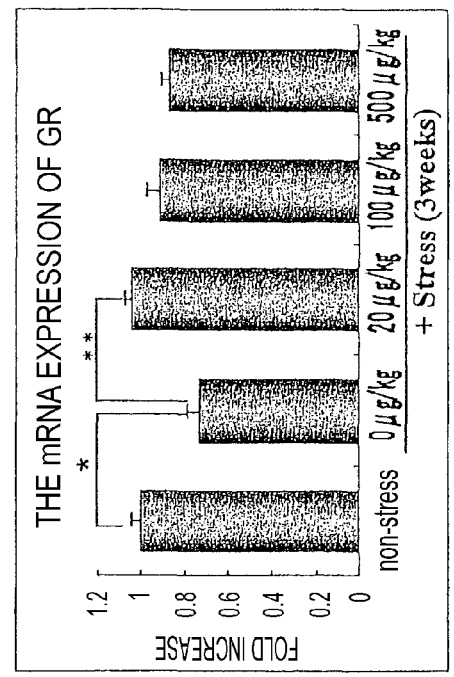
Figure 15:
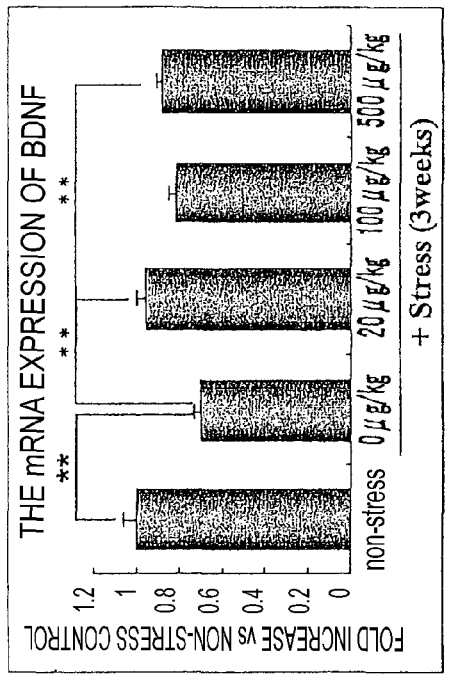
Figure 15:
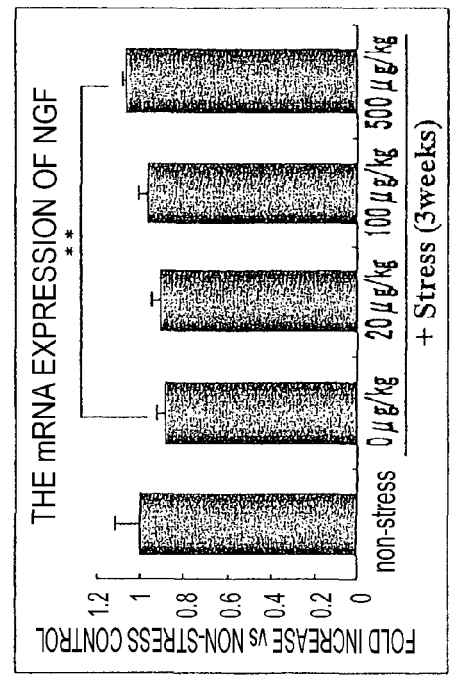
Figure 16:
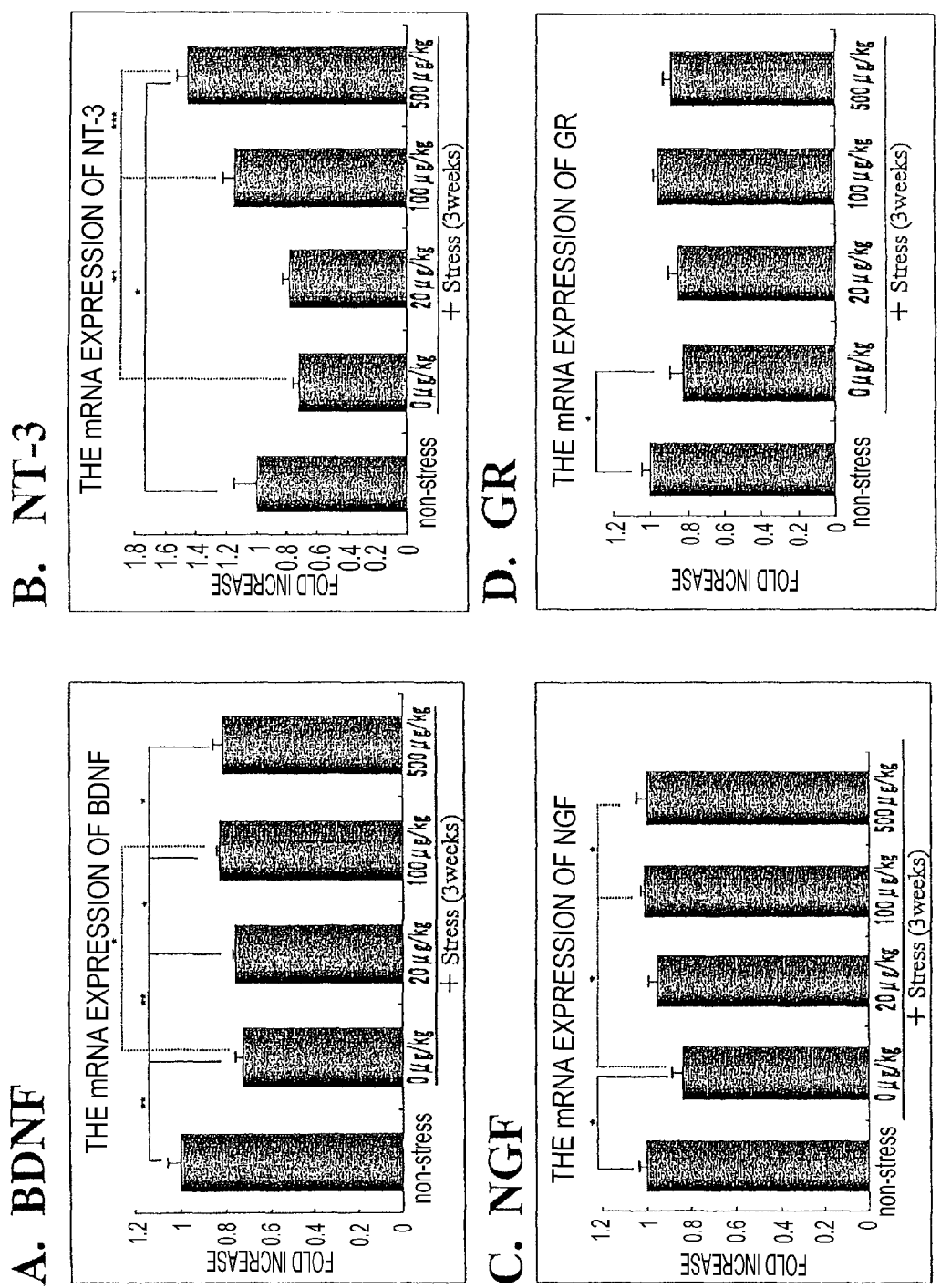
FIG. 16 is a graph comparing expression amounts of mRNAs of BDNF, NT-3, NGF and GR in hippocampi between stressed examples obtained by administering the compound 8 and applying stress for 3 weeks and non-stressed examples in Example 5.
Figure 17:
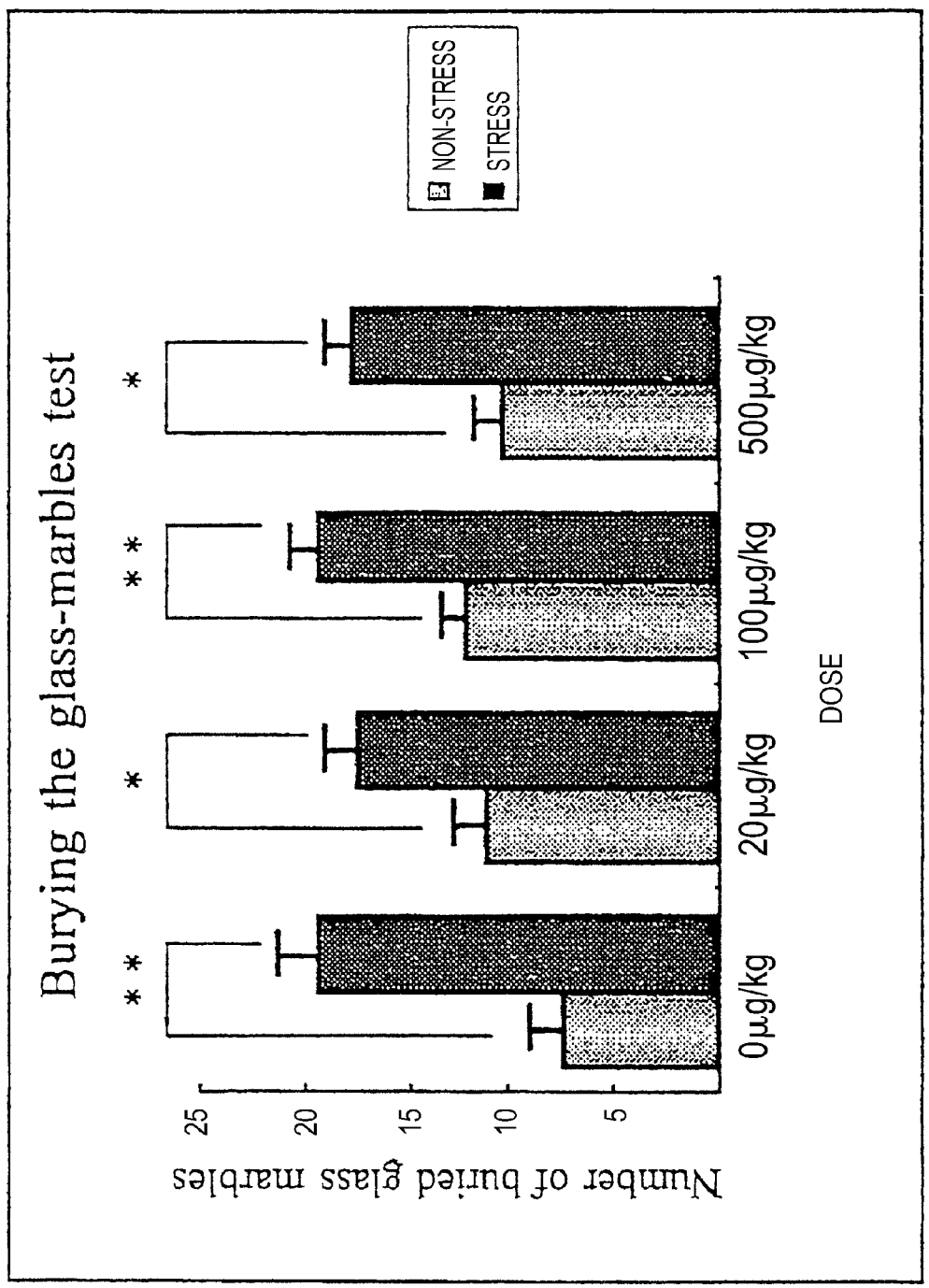
FIG. 17 is a graph of a burying the glass-marbles test of comparing the numbers of buried glass marbles between stressed examples and non-stressed examples of the "non-administration groups after completion of stress" in Example 6.

The obtained precipitate was washed with 70% ethanol, dried and then dissolved in TE to form a total RNA sample. For reverse transcription of RNA, annealing was performed by adding a CDS primer (oligo dt primer) solution to 0.5 µg of the total RNA sample to react at 72° C. for 2 minutes. Then, a 5×first strand buffer, DTT, dNTP and a reverse transcriptase were added thereto to react at 42° C. for 60 minutes. Thereto was added TE and reacted at 72° C. for 7 minutes to form a cDNA sample. A PCR reaction was carried out by adding a mixed solution containing cDNA, Tag polymerase and primers (respective primers having sequences (10 to 20) specific to BDNF, NGF, NT-3 and GR). In the PCR reaction, a treatment was carried out at 94° C. for 5 minutes in initiation, modification at 94° C. for 45 seconds, annealing at 61° C. for 45 seconds, and elongation at 72° C. for 30 seconds were performed as one cycle, 28 cycles were repeated for BDNF, 30 cycles were repeated for NT-3, 34 to 37 cycles were repeated for NGF, and 37 cycles were repeated for GR. At last, an elongation reaction was performed at 72° C. for 7 minutes. After the PCR reaction, electrophoresis was carried out with a 2% agarose gel and an amplified DNA fragment was subjected to fluorescent color development of a band with ethidium bromide. The fluorescence intensity of the band was read with a densitometer to digitalize and the obtained value was divided with a fluorescence intensity of a band of RT-PCR of β actin mRNA of an internal standard, which has been found separately, and a graph was formed assuming that the band value of a non-stressed mouse/β actin band value was 1.0. FIGS. 15 and 16 show the results.

Expressions of mRNAs of BDNF, NT-3 and GR in the cortexes of frontal lobes were significantly decreased in controls (0 µg/kg) as compared to non-stressed examples (see FIG. 15), and Expressions of mRNAs of BDNF, NGF and GR in the hippocampi were significantly decreased in controls (0 µg/kg) as compared to non-stressed examples (see FIG. 16). Since it has already been known that expressions of mRNAS of GR and BDNF are lowered, stress of the test provoking reduction in expression of mRNAs of BDNF and GR is determined to be homogeneous to conventionally reported stress. In FIGS. 15 and 16, since mRNAs of BDNF, NT-3, NGF and GR were returned to the level of non-stressed examples in the compound 8 administration examples, reduction in expression of neurotrophic factor related genes accompanied by stress was suppressed with the compound 8, and considered to be improved to a state of a non-stressed example.

Example 6

Behavior Test of Mice after Completion of Stress

Example 2 is a behavior test in which the compound 8 was administered to a mouse as well as stress was applied and a suppression effect of the compound 8 on depressive and anxiety symptoms of the mouse was examined. On the other hand, the present example is a behavior test in which only stress was applied for 3 weeks without administering the compound 8 and stress was completed and a therapeutic effect of the compound 8 on depressive and anxiety symptoms of a mouse after removing stress was examined. Stress was applied to a mouse in the same manner as in Example 2. For behavior tests of mice, the burying the glass-marbles test, the tail suspension test and the elevated plus maze test were performed respectively in the same manners as in Example 2 on groups without administering the compound 8 immediately after completion of stress for 3 weeks and groups without administering the compound 8 with no stress from the start (hereinafter referred to as "non-administration groups after completion of stress"); a group administered with the compound 8 for 1 week after completion of stress and a group administered with the compound 8 for 1 week in the same manner as the former group with no stress from the start (hereinafter referred to as "1 week-administration groups after completion of stress"); and a group administered with the compound 8 for 2 weeks after completion of stress and a group administered with the compound 8 for 2 weeks in the same manner as the former group with no stress from the start (hereinafter referred to as "2 week-administration groups after completion of stress"). In any of the following behavior tests of mice, there were significant differences between a stressed example and a non-stressed example of controls (0 μg/kg) of "the non-administration groups after completion of stress" and between a stressed example and a non-stressed example of the compound 8 administration groups (see FIGS. 17, 20 and 23). Although doses are described in FIGS. 17, 20, 23 and 24 showing "the non-administration groups after completion of stress", the compound 8 was not administered in any of the groups as described above, and mice corresponding to each of the administration groups, "the 1 week-administration groups after completion of stress" and "the 2 week-administration groups after completion of stress" are only shown.

1. Burying the Glass-Marbles Test

Figure 18:
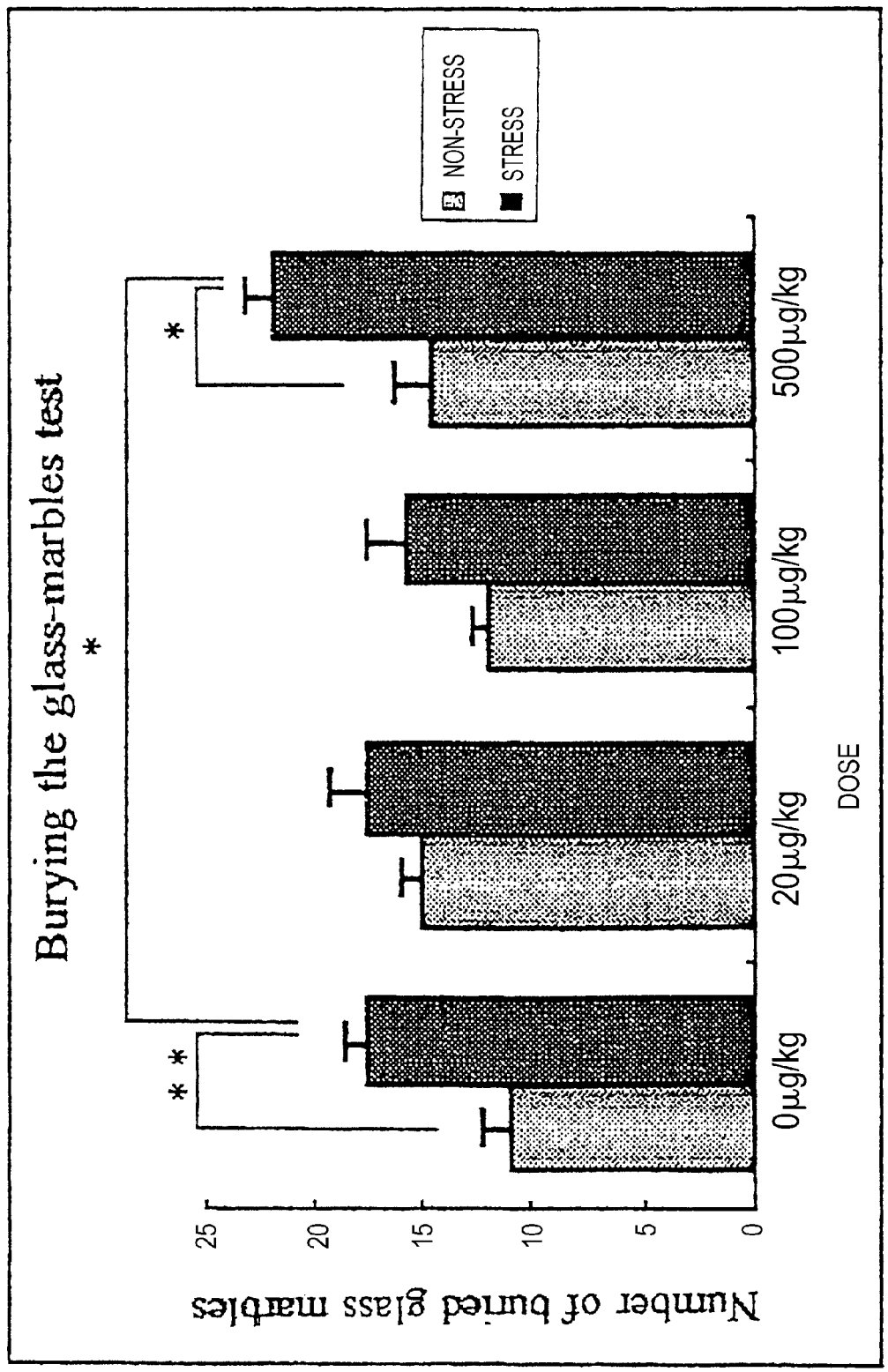
FIG. 18 is a graph of a burying the glass-marbles test of comparing the numbers of buried glass marbles between stressed examples and non-stressed examples of the "1 week-administration groups after completion of stress" in Example 6.
Figure 19:
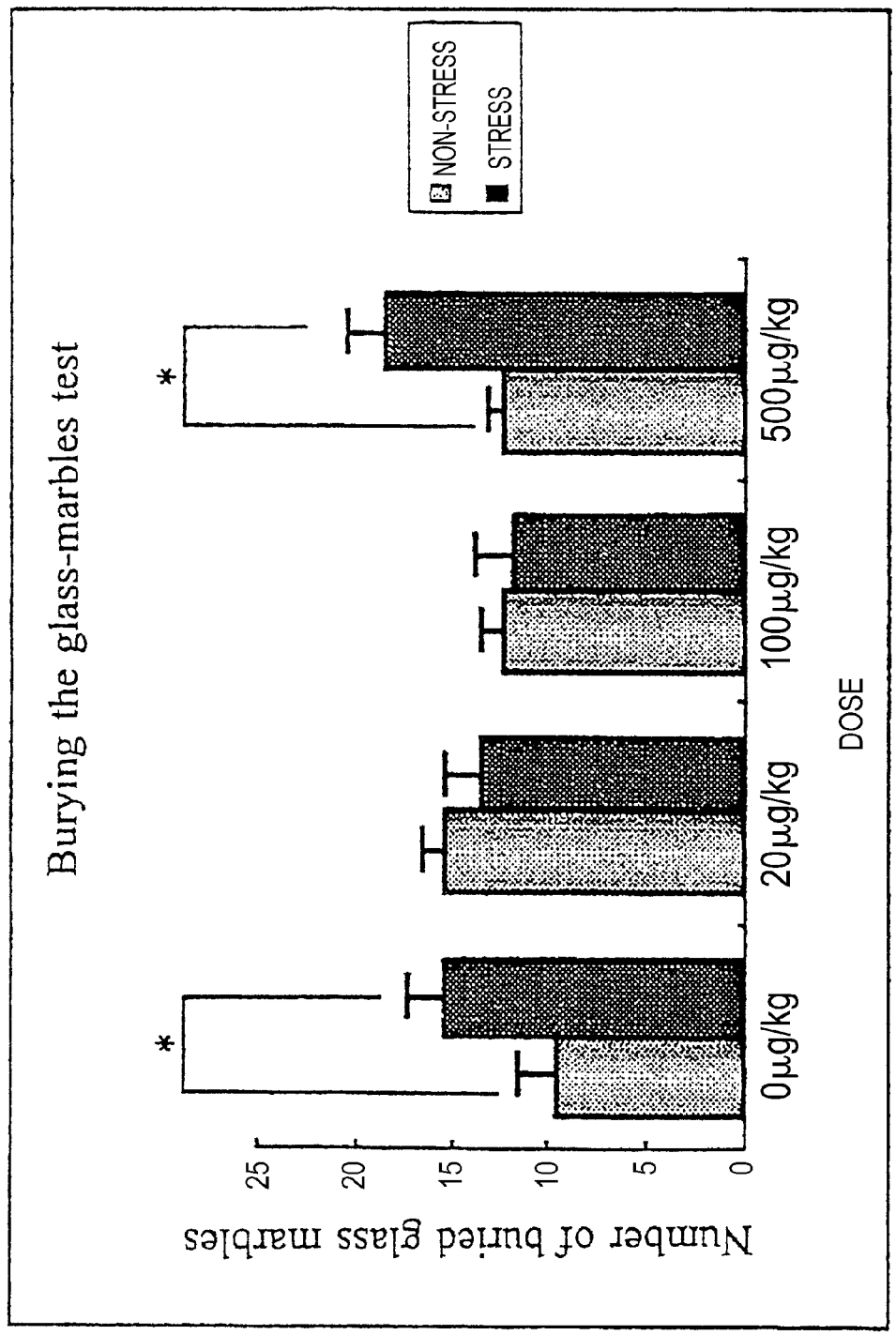
FIG. 19 is a graph of a burying the glass-marbles test of comparing the numbers of buried glass marbles between stressed examples and non-stressed examples of the "2 week-administration groups after completion of stress" in Example 6.
Figure 20:
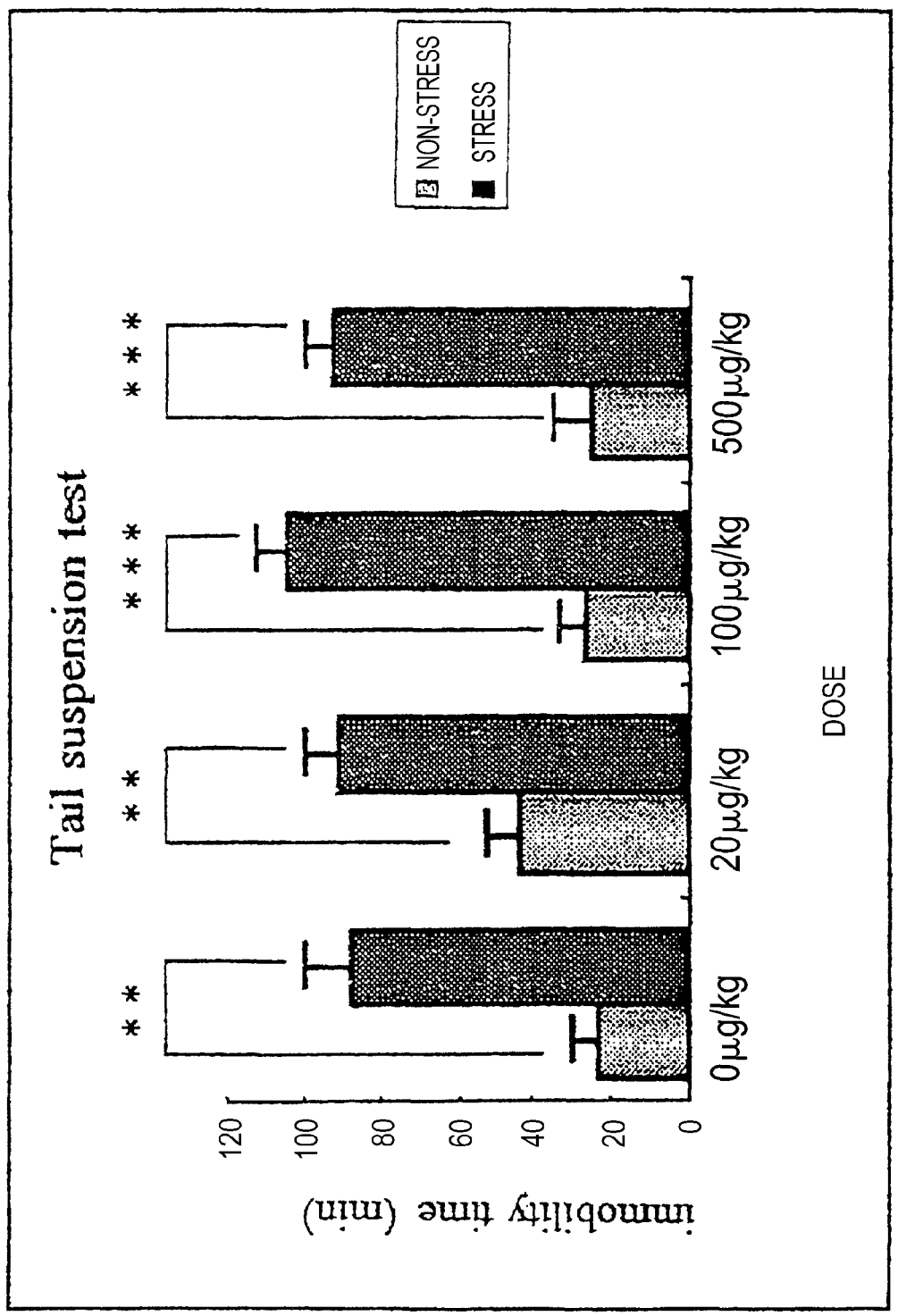
FIG. 20 is a graph of a tail suspension test of comparing immobility times between stressed examples and non-stressed examples of the "non-administration groups after completion of stress" in Example 6.

The numbers of glass marbles buried by mice had a significant difference between a stressed example and a non-stressed example of controls (0 μg/kg) in any of "the 1 week-administration groups after completion of stress" and "the 2 week-administration groups after completion of stress"; on the other hand, there was no significant difference between a stressed example and a non-stressed example in each administration example of 20 μg/kg and 100 μg/kg (see FIGS. 18 and 19), and the compound 8 exhibited a therapeutic effect on an anxiety symptom after stress was removed. The result of "the 1 week-administration groups after completion of stress", the compound 8 is considered to have an immediate therapeutic effect on the anxiety symptom.

2. Tail Suspension Test

Figure 21:
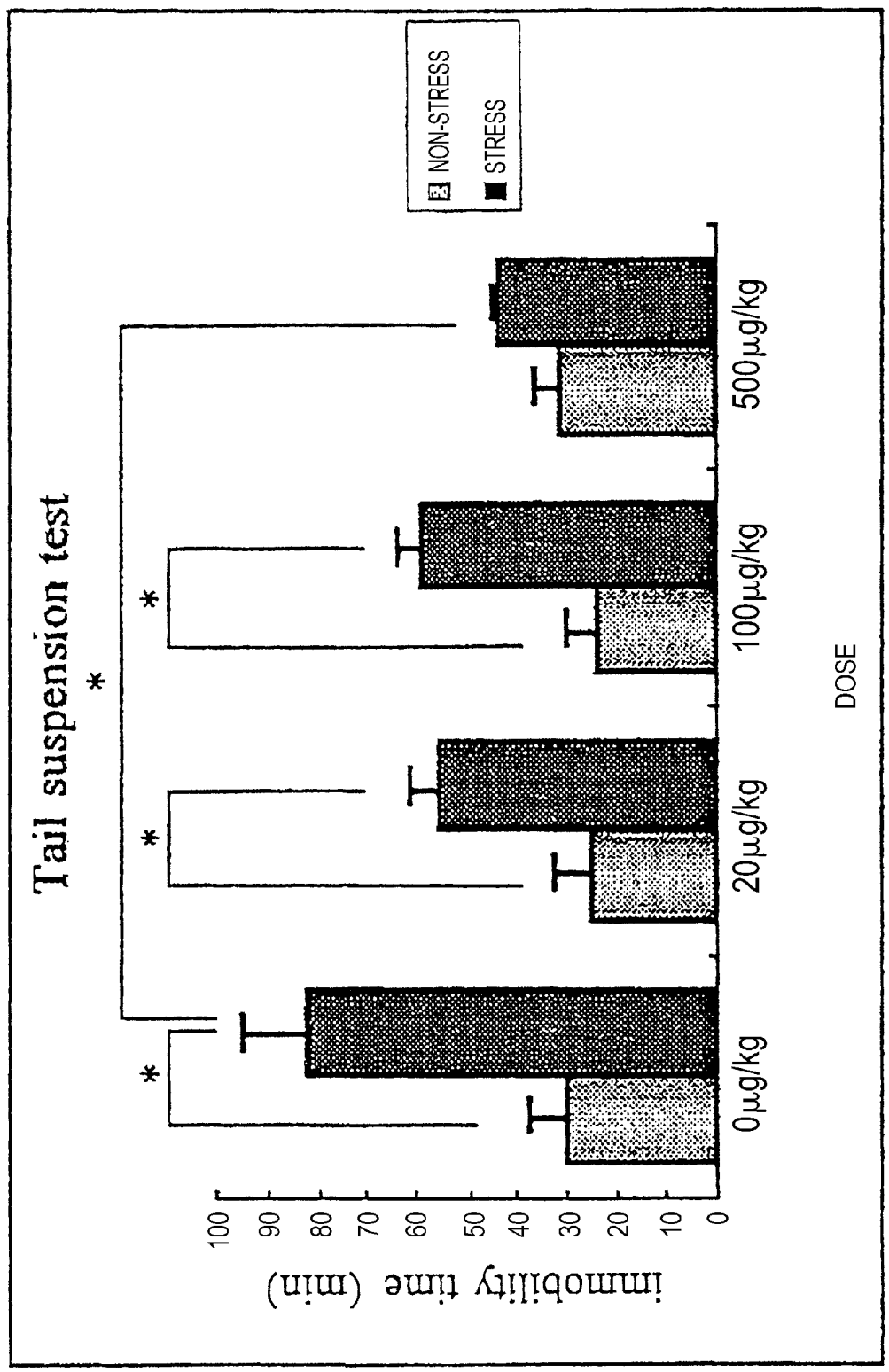
FIG. 21 is a graph of a tail suspension test of comparing immobility times between stressed examples and non-stressed examples of the "1 week-administration groups after completion of stress" in Example 6.
Figure 22:
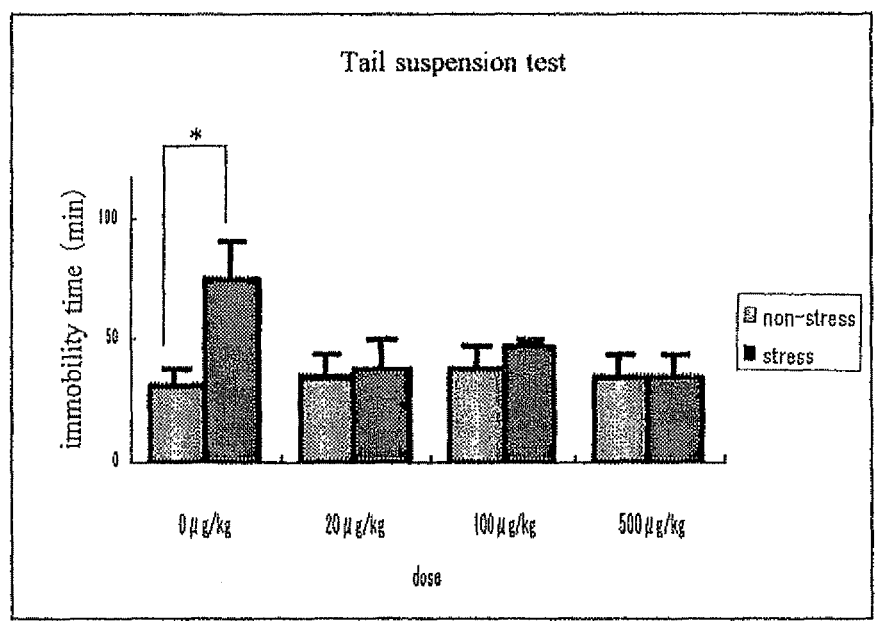
FIG. 22 is a graph of a tail suspension test of comparing immobility times between stressed examples and non-stressed examples of the "2 week-administration groups after completion of stress" in Example 6.
Figure 23:
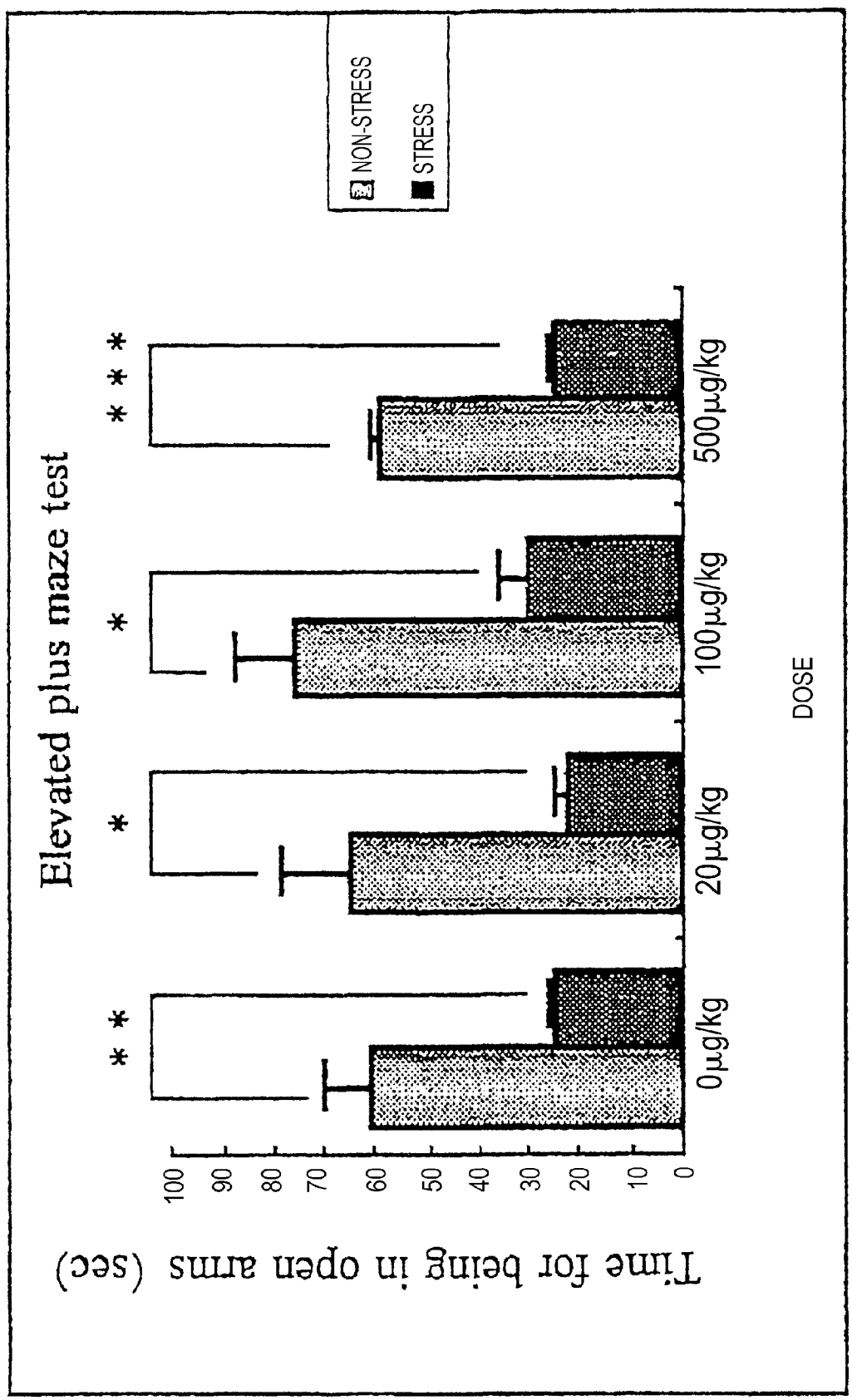
FIG. 23 is a graph of an elevated plus maze test of comparing times for being in open arms between stressed examples and non-stressed examples of the "non-administration groups after completion of stress" in Example 6.
Figure 24:
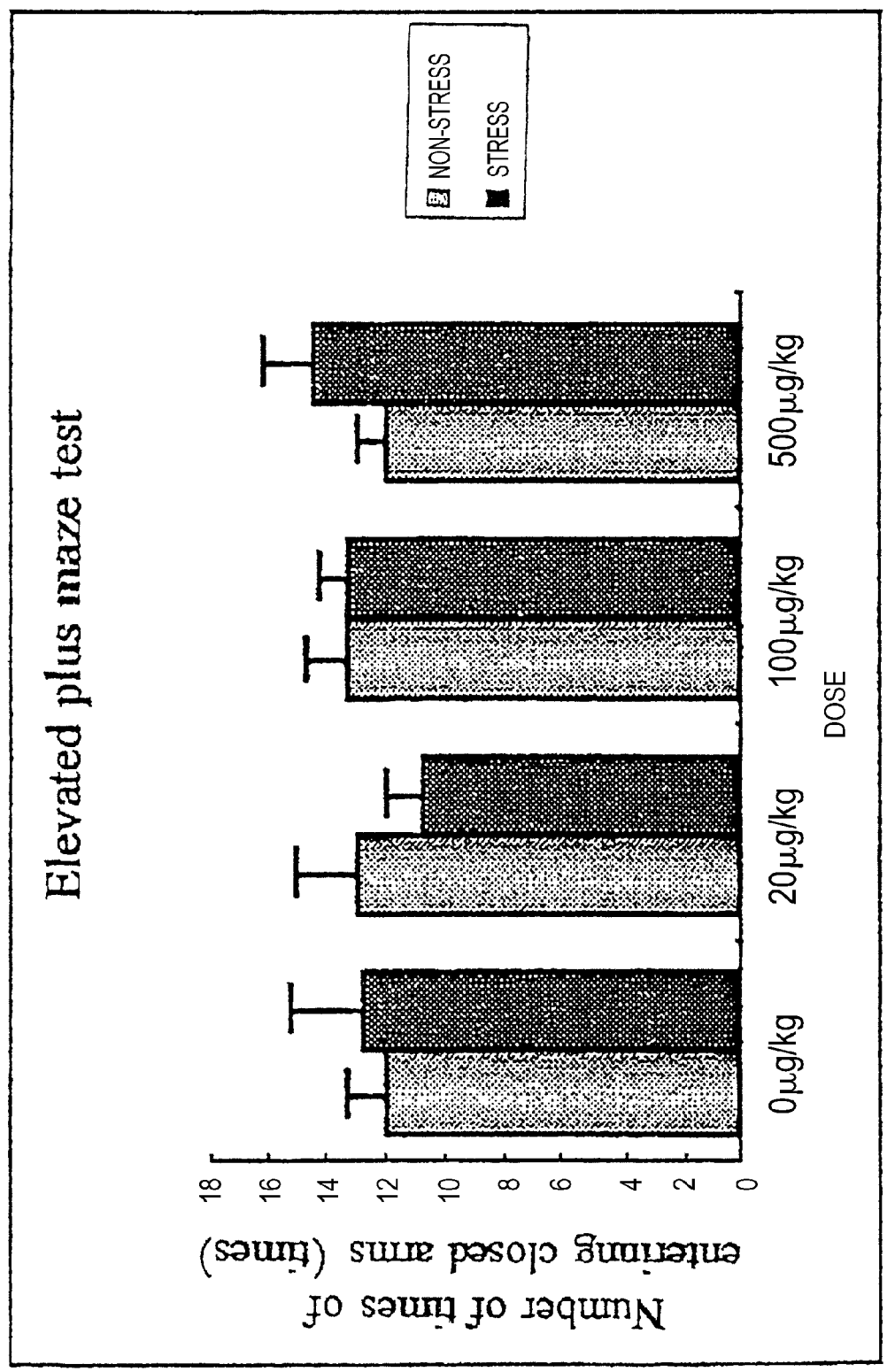
FIG. 24 is a graph of an elevated plus maze test of comparing the numbers of times of entering closed arms between stressed examples and non-stressed examples of the "non-administration groups after completion of stress" in Example 6.

The immobility times of mice had a significant difference between a stressed example and a non-stressed example of controls (0 μg/kg) in "the 1 week-administration groups after completion of stress", but there was no significant difference between a stressed example and a non-stressed example in 500 μg/kg administration examples (see FIG. 21), and the compound 8 exhibited an immediate therapeutic effect on an anxiety symptom after removing stress. The immobility times of mice had a significant difference between a stressed example and a non-stressed example of controls (0 μg/kg) in "the 2 week-administration groups after completion of stress", but there was no significant difference between a stressed example and a non-stressed example in all administration examples (see FIG. 22), and the compound 8 exhibited a high therapeutic effect on a depressive symptom after removing stress.

3. Elevated Plus Maze Test

Figure 25:
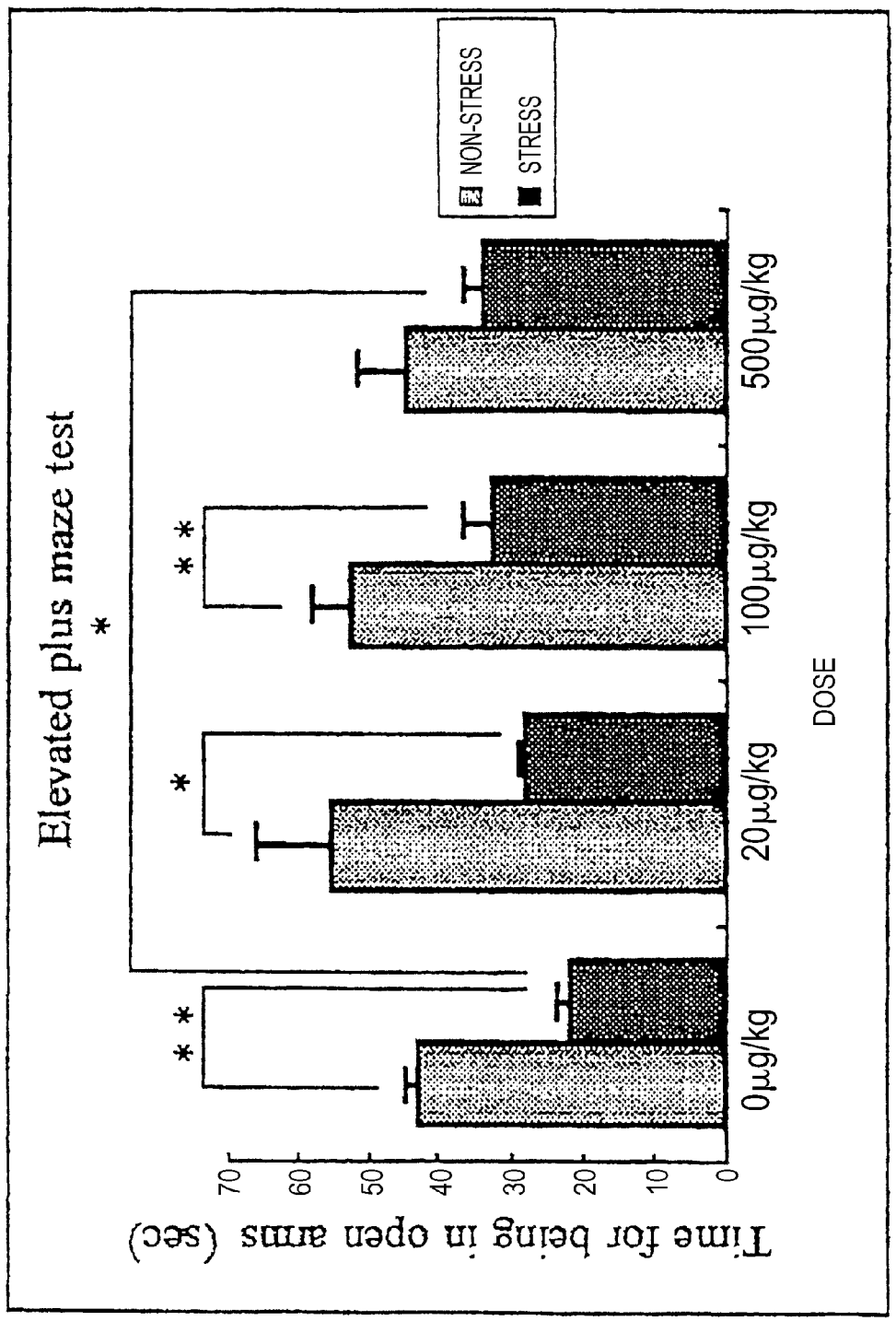
FIG. 25 is a graph of an elevated plus maze test of comparing times for being in open arms between stressed examples and non-stressed examples of the "1 week-administration groups after completion of stress" in Example 6.
Figure 26:
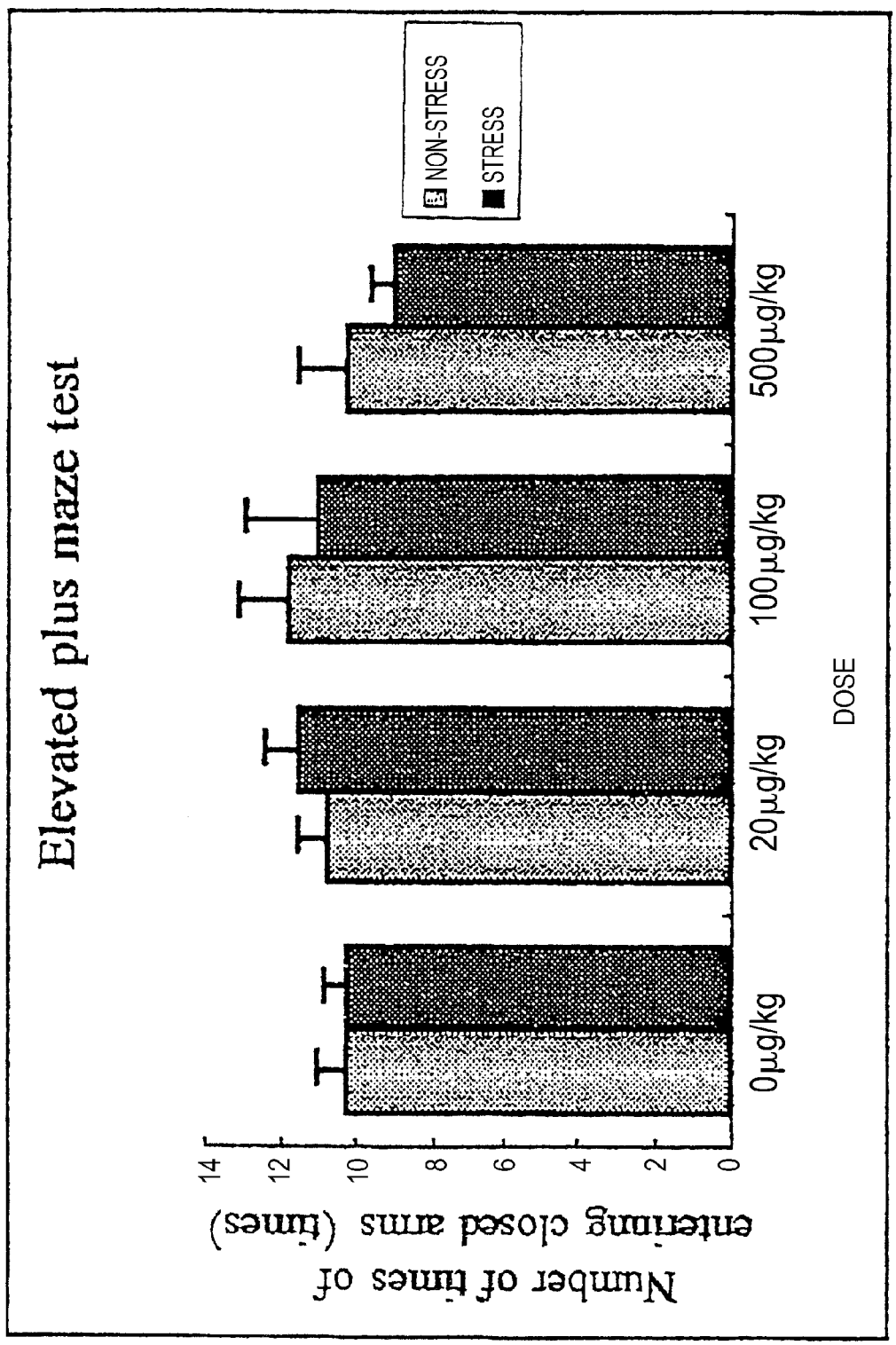
FIG. 26 is a graph of an elevated plus maze test of comparing the numbers of times of entering closed arms between stressed examples and non-stressed examples of the "1 week-administration groups after completion of stress" in Example 6.
Figure 27:
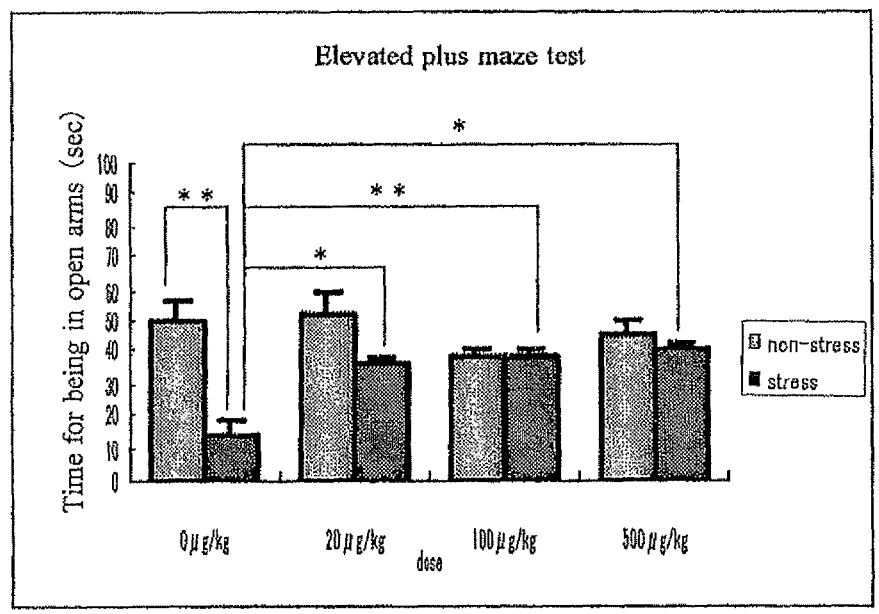
FIG. 27 is a graph of an elevated plus maze test of comparing times for being in open arms between stressed examples and non-stressed examples of the "2 week-administration groups after completion of stress" in Example 6.
Figure 28:
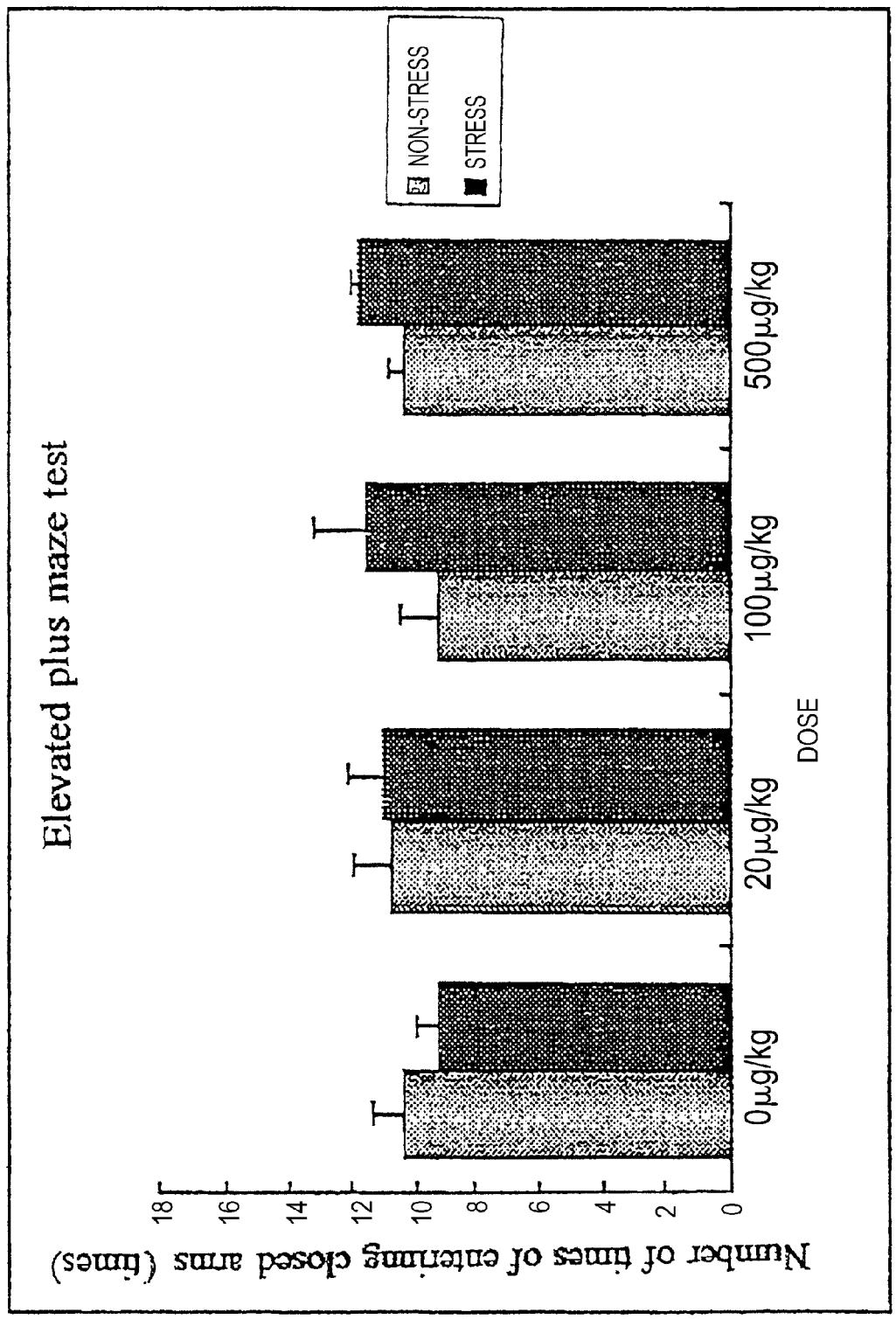
FIG. 28 is a graph of an elevated plus maze test of comparing the numbers of times of entering closed arms between stressed examples and non-stressed examples of the "2 week-administration groups after completion of stress" in Example 6.

Since the numbers of times when mice enter the closed arm had no significant difference between controls (0 μg/kg) and the compound 8 administration groups and between stressed groups and non-stressed groups in any of "the non-administration group after completion of stress", "the 1 week-administration groups after completion of stress" and "the 2 week-administration groups after completion of stress" (see FIGS. 24, 26 and 28), administration of the compound 8 did not give an effect on behavior amounts of the mice, and thus, the times when the mice are in the open arm do not depend on the behavior amounts. The times when the mice were in the open arm had a significant difference between a stressed example and a non-stressed example of the controls (0 μg/kg) in "the 1 week-administration groups after completion of stress", but there was no significant difference between a stressed example and a non-stressed example of the 500 μg/kg administration examples (see FIG. 25), and the compound 8 exhibited an immediate therapeutic effect on an anxiety symptom after stress was removed. There was a significant difference between a stressed example and a non-stressed example of the controls (0 μg/kg) in "the 2 week-administration group after completion of stress", but there was no significant difference between stressed examples and non-stressed examples of all administration examples (see FIG. 27), and the compound 8 exhibited a high therapeutic effect on an anxiety symptom after stress was removed.

Example 7

Measurement of Weights of Mice after Completion of Stress

Figure 29:
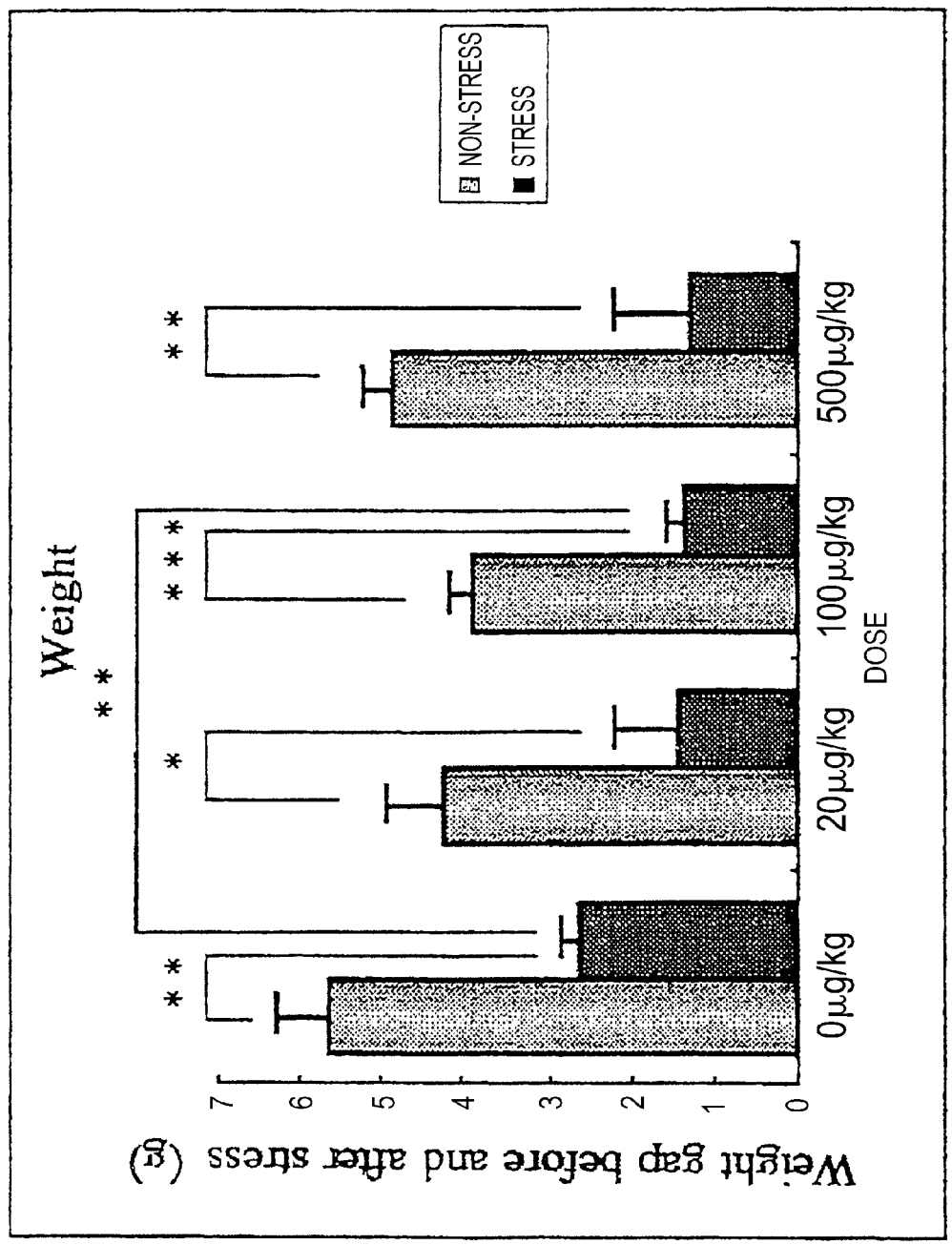
FIG. 29 is a graph comparing gaps of body weights between stressed examples immediately after applying stress for 3 weeks and non-stressed examples in Example 7.
Figure 30:
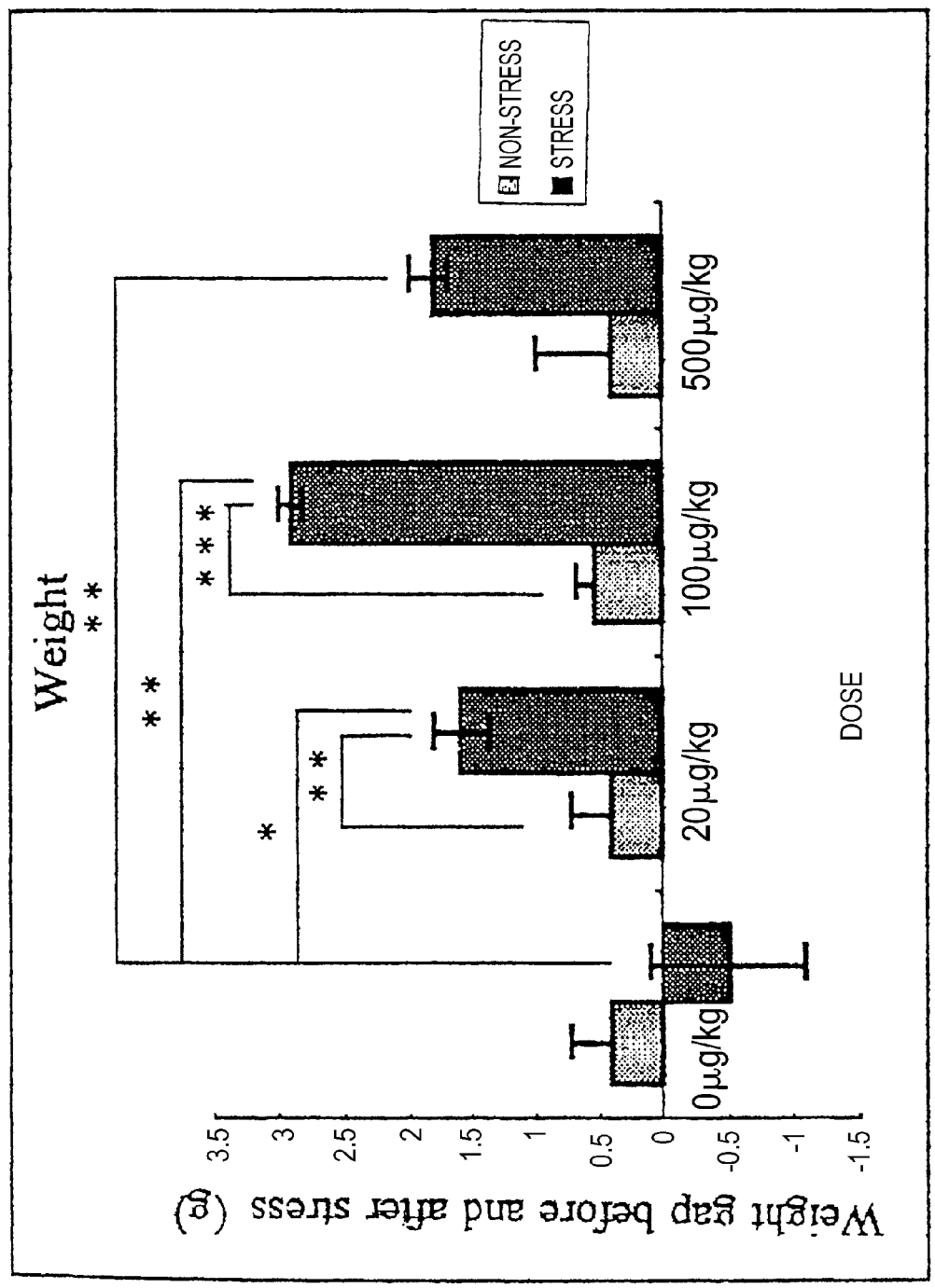
FIG. 30 is a graph comparing gaps of body weights between stressed examples obtained by administering the compound 8 for 1 week after applying stress for 3 weeks and non-stressed examples in Example 7.

A weight of a mouse before stress was subtracted from of the weight of the mouse immediately after completion of stress for 3 weeks without administering the compound 8 and the weight of the mouse after administering the compound 8 for 1 week after completion of stress, respectively, to obtain weight gaps (g). FIGS. 29 and 30 show the results. Although doses are described in FIG. 29, the compound 8 was not administered as described above, and mice corresponding to each of the administration groups administered with the compound 8 for 1 week after completion of stress are only shown.

From FIG. 29, the weight gaps of mice immediately after completion of stress had significant differences between a stressed example and a non-stressed example of the controls (0 μg/kg) and between stressed examples and non-stressed examples corresponding to respective administration groups, but in the 500 μg/kg administration examples after administrating the compound 8 for 1 week after completion of stress, there was no significant difference between a stressed example and a non-stressed example due to a therapeutic effect of the compound 8 on repressive and anxiety symptoms.

Example 8

Figure 31:
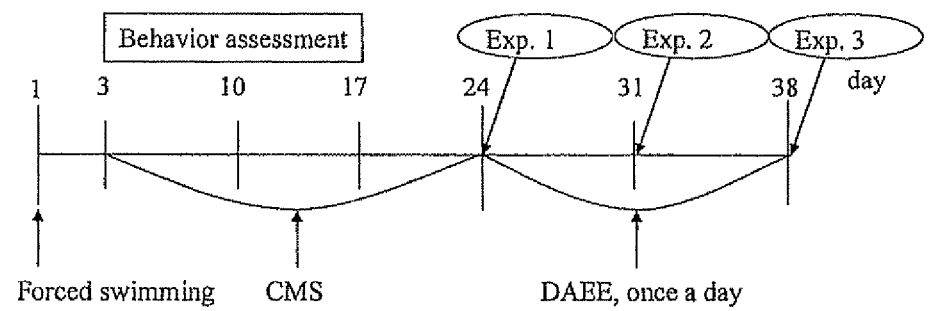
FIG. 31 show an evaluation method of a behavior test (behavior assessment) (A) and a graph of a tail suspension test (B) comparing effects on antidepressant symptoms with the compound 8 and fluvoxamine in Example 8.
Figure 31:
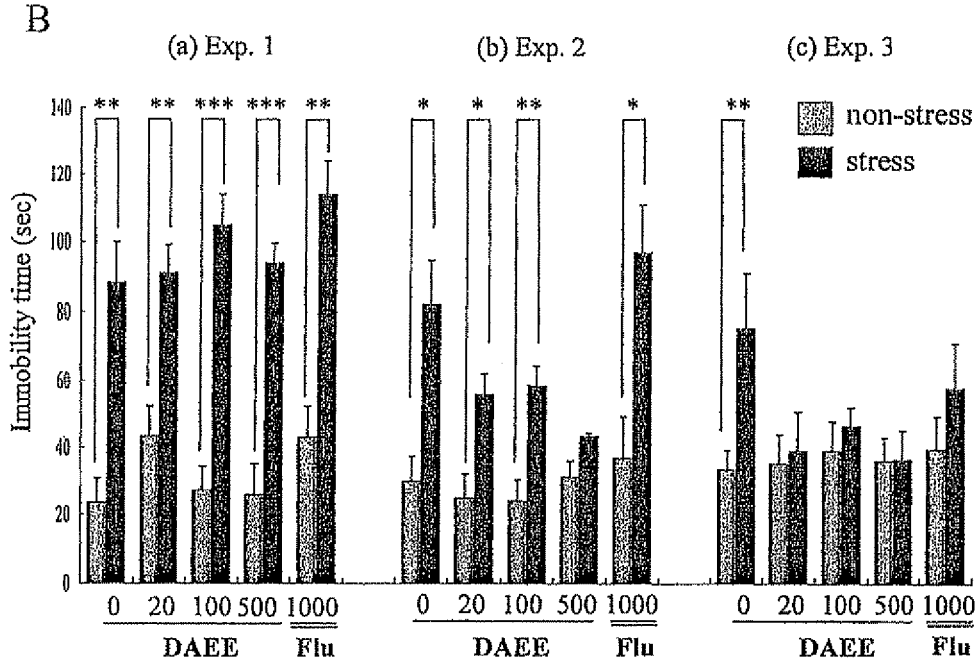

Comparison of Effects of Compound 8 and Fluvoxamine on Depressive Symptom in Tail Suspension Test 7-week-old male ddY strain mice fed in one cage for 4 mice were first subjected to forced swimming for 15 minutes in the same manner as stress in Example 2 (behavior test of mice under stress) (1) described in the paragraph [0063] in the specification. Then, stress for 1 week using 3 kinds of cages was regarded as 1 cycle, and the stress was applied for 3 cycles (3 weeks) and chronic mild stress (CMS) was applied. The compound 8 and fluvoxamine were administered to mice immediately after stress in Exp. 1, 1 week after stress in Exp. 2, and 2 weeks after stress in Exp. 3, respectively, and tail suspension tests were carried out on the respective test groups. In each test group, the compound 8 was adjusted in concentration so as to have each of the doses of 20, 100 and 500 tag/kg and fluvoxamine was adjusted in concentration so as to have a dose of 1000 µg/kg, by dissolving in 0.1% DMSO, and each dose of the compound 8 and fluvoxamine were intraperitoneally injected to mice once per day from the time immediately after stress. Further, to 7-week-old male ddY strain mice fed in one cage for 4 mice without stress, the compound 8 and fluvoxamine were administered to carry out the tail suspension tests in the same manner as the stressed mice. FIG. 31 show the result. A significance test was performed in a Student's t-test (*). FIG. 31A shows an evaluation method of the behavior test (behavior assessment). FIG. 31B shows immobility times of the mice. "DAEE" denotes the compound 8 and "Flu" denotes fluvoxamine.

FIG. 31B reveals that the compound 8 had an effect in a dose of 500 µg/kg in Exp. 2 (1 week after stress) but an effect could not be recognized with fluvoxamine. An effect of fluvoxamine was recognized only in Exp. 3 (2 weeks after stress). The results found that the compound 8 was excellent in an effect on a depressive symptom.

Example 9

Voluntary Alternation Behavior Test of Mice Administered with Trimethyltin (Y-Maze Test)

The voluntary alternation behavior test (Y-maze test) is one kind of a behavior test using a Y-shaped maze constituted with three arms. First, a mouse is placed on the tip of one arm out of the three arms, letting the mouse freely explore in the maze over 8 minutes, and arms where the mouse transferred are recorded in order. Then, the number of times of transferring to each arm (total arm selection number (total arm entries)) and the number of sequentially selecting three different arms (number of alternation behavior (number of spontaneous behavior)) are counted. A normal mouse shows a high probability that indicates a behavior of transfer with selecting three different arms, and a mouse with declined memory and learning abilities shows a low probability of taking such a behavior, and thus, number of spontaneous behavior÷(total arm entries−2)×100=alternation behavior (%) was calculated to be the index of the voluntary alternation behavior.

Trimethyltin (hereinafter referred to as "TMT") is an organic metal compound having neurotoxicity, and acute nerve cell death is cased particularly in granular nerve cells of the hippocampus dentate gyrus, which thus affects memory and learning abilities of a mouse. Therefore, TMT is administered to a mouse, and the alternation behavior (%) is significantly decreased.

Figure 32:
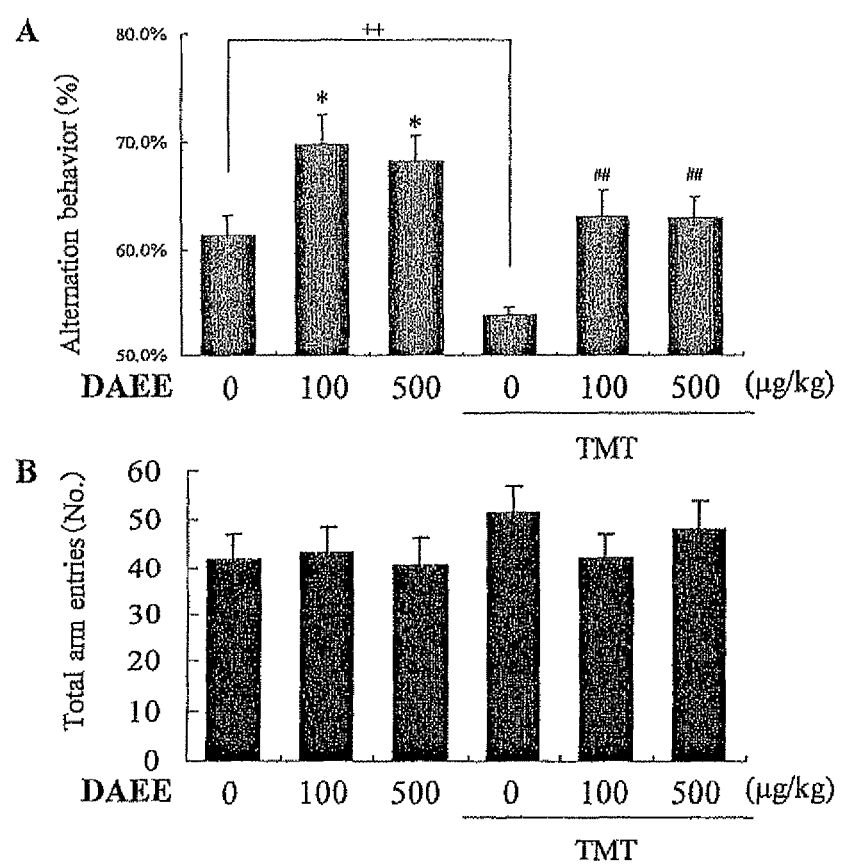
FIG. 32 are graphs of a voluntary alternation behavior test (Y-maze test) of mice administered with trimethyltin in Example 9.

The voluntary alternation tests (Y-maze tests) were performed on 1) test groups to which the compound 8 was singly administered and 2) test groups to which TMT and the compound 8 were administered. In the test groups to which the compound 8 was singly administered, the compound 8 was dissolved in 0.1% DMSO to adjust a concentration so as to have each of the doses of 100 and 500 µg/kg and intraperitoneally injected to 6 mice in every administration example each in a dose of 0.25 mL. In 0 µg/kg weight administration examples of controls, 0.25 mL of a phosphoric acid buffer containing 0.1% DMSO was intraperitoneally injected in each time. The voluntary alternation tests (Y-maze tests) were performed on each of the administration groups after the elapse of 2 hours from intraperitoneal administration. In the test group in which TMT and the compound 8 were administered, TMT (2 mg/kg weight) was intraperitoneally administered to a mouse, and the compound 8 was intraperitoneally administered in the same manner as the test groups in which the compound 8 was singly administered after 2 days have passed, and the voluntary alternation test (Y-maze test) was performed after the elapse of 2 hours. FIG. 32 show the results. Significance tests were performed in a Turkey's test (*, ##) and a Student's t-test (++). "DAEE" denotes the compound 8.

According to FIG. 32B, the total arm entries had no difference among respective test groups, which means that there was no difference in motor functions of the respective test groups. FIG. 32A reveals that, in the test examples in which TMT and the compound 8 were administered at the same time, administration of the compound 8 suppressed decrease in the voluntary alternation behaviors that significantly decreased due to TMT treatments. On the other hand, it was found that, also in the test examples in which the compound 8 was singly administered, the voluntary alternation behaviors significantly increased due to administration of the compound 8, and thus, the compound 8 can impart resistivity against neurotoxicity of TMT to suppress declined memory and learning abilities and to promote the memory and leaning abilities of mice. From the above respects, the compound 8 is considered to have an activity of improving memory and learning abilities by further increasing general functions of the hippocampus. Such an activity is considered to give a suppressive effect also on declined nervous functions due to an amyloid β peptide in Alzheimer's disease.

Example 10

Novel Object Recognition Test on Mice

A promotion activity of brain functions due to the compound 8 was examined using a novel object recognition test. The novel object recognition test is a method of evaluating memory and learning abilities from behaviors after showing a "familiar object" and a "novel object" to mice, utilizing the fact that the mice take exploration behaviors (behaviors such as coming closer to or smelling an object) when they find the "novel object".

Figure 33:
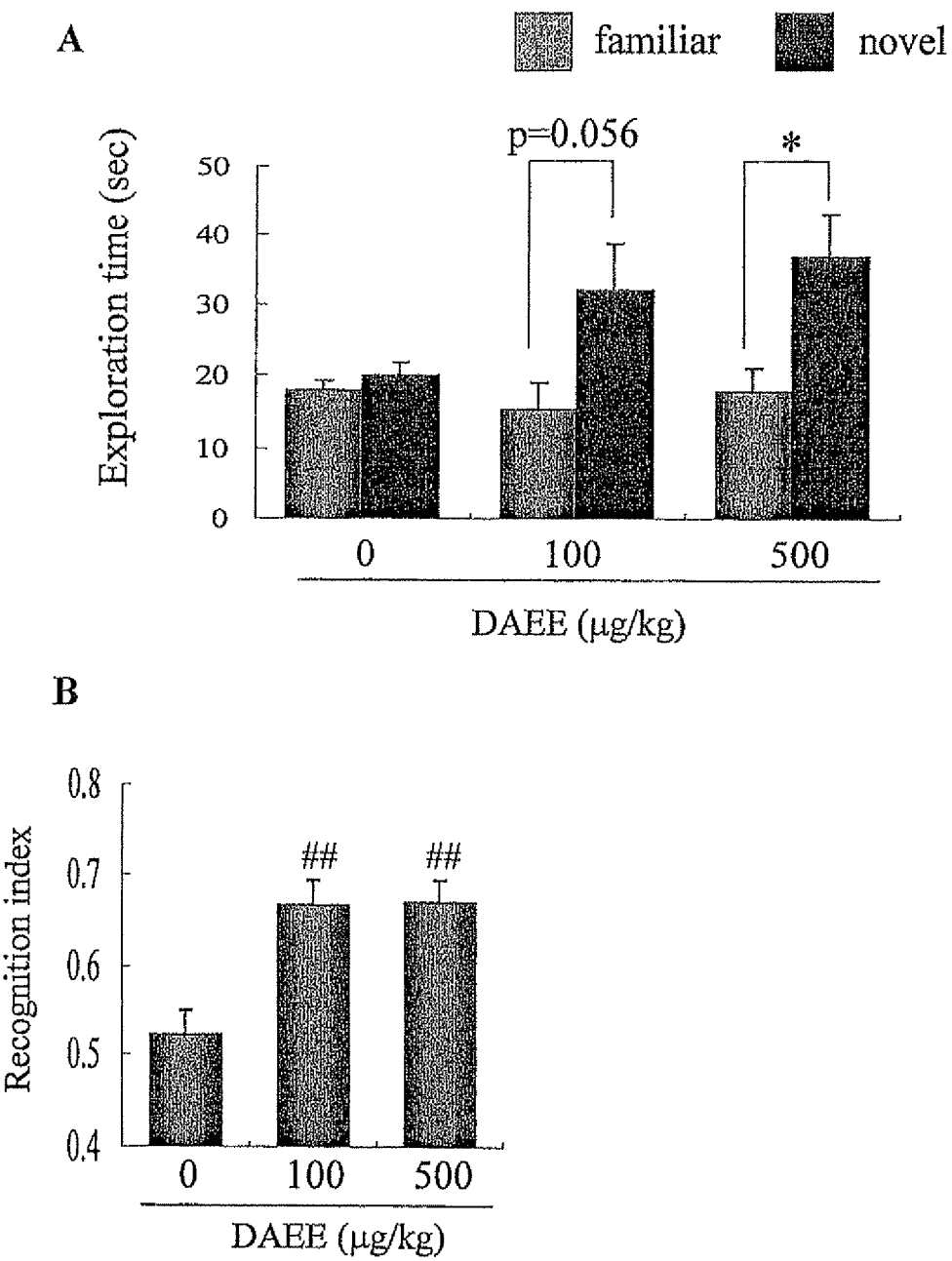
FIG. 33 are graphs of a novel object recognition test of mice in Example 10.

The compound 8 was dissolved in 0.1% DMSO to adjust a concentration so as to have each dose of 100 and 500 µg/kg and intraperitoneally injected to 6 mice in every administration example each in a dose of 0.25 mL. In a 0 µg/kg weight administration example of a control, 0.25 mL of a phosphoric acid buffer containing 0.1% DMSO was intraperitoneally injected. The compound 8 was administered to mice and the novel object recognition test was performed after 2 hours. That is, a mouse was put in a place where two identical objects were present for 15 minutes to let the mouse memorize the two objects (these two objects will be "familiar objects"). After the elapse of 1 day, an exploration behavior test in which the mouse was put in a place where the "familiar objects and "novel objects" were present was carried out for 10 minutes FIG. 33 show the results. Significance tests were performed in a Student's t-test (*) and a Turkey's test (##). "DAEE" denotes the compound 8.

FIG. 33A shows time for the mice to explore "familiar objects" and "novel objects" (exploration time). FIG. 33B shows recognition indices. The recognition indices are expressed by Y/X+Y assuming that a time for exploring the "familiar objects" is X and a time for exploring the "novel objects" is Y. It was found from FIG. 33B that since the recognition indices of the "novel objects" became high in examples to which the compound 8 was administered, the compound 8 had an activity of enhancing memory and learning abilities of a healthy animal. Such an activity is considered to give a suppressive effect also on declined nervous functions due to an amyloid β peptide in Alzheimer's disease.

The invention claimed is:

1. A method of activating MAP kinases, comprising administering an ester of a decenoic acid to nerve cells, wherein the ester of the decenoic acid is selected from the group consisting of trans-2-decenoic acid ethyl ester, trans-2-decenoic acid methyl ester, trans-2-decenoic acid-trans-2-decenyl ester, trans-2-decenoic acid cyclohexyl ester, trans-2-decenoic acid octyl ester, trans-2-decenoic acid isopropyl ester, trans-3-decenoic acid methyl ester, trans-3-decenoic acid ethyl ester, trans-9-decenoic acid methyl ester, and trans-9-decenoic acid ethyl ester.

2. The method of claim 1, wherein the ester of the decenoic acid is selected from the group consisting of trans-2-decenoic acid ethyl ester, trans-2-decenoic acid methyl ester, trans-2-decenoic acid-trans-2-decenyl ester, trans-2-decenoic acid cyclohexyl ester, trans-2-decenoic acid octyl ester, and trans-2-decenoic acid isopropyl ester.

3. The method of claim 1, wherein the ester of the decenoic acid is selected from the group consisting of trans-2-decenoic acid ethyl ester, trans-2-decenoic acid methyl ester, trans-2-decenoic acid-trans-2-decenyl ester, trans-2-decenoic acid cyclohexyl ester, trans-2-decenoic acid isopropyl ester, and trans-9-decenoic acid methyl ester.

4. The method of claim 1, wherein the ester of the decenoic acid is trans-2-decenoic acid ethyl ester.

5. A method for treating depression or anxiety disorder (neurosis), comprising administering a therapeutically effective amount of a pharmaceutical preparation comprising, as an active ingredient, an ester of a decenoic acid to a person in need thereof, wherein the ester of the decenoic acid is selected from the group consisting of trans-2-decenoic acid ethyl ester, trans-2-decenoic acid methyl ester, trans-2-decenoic acid-trans-2-decenyl ester, trans-2-decenoic acid cyclohexyl ester, trans-2-decenoic acid isopropyl ester, and trans-9-decenoic acid methyl ester.

6. The method of claim 5, wherein the method treats depression.

7. The method of claim 5, wherein the method treats anxiety disorder (neurosis).

8. The method of claim 5, wherein the ester of the decenoic acid is trans-2-decenoic acid ethyl ester.

9. A method for treating Alzheimer's disease, comprising administering a therapeutically effective amount of a pharmaceutical preparation comprising, as an active ingredient, an ester of a decenoic acid to a person in need thereof, wherein the ester of the decenoic acid is selected from the group consisting of trans-2-decenoic acid ethyl ester, trans-2-decenoic acid methyl ester, trans-2-decenoic acid-trans-2-decenyl ester, trans-2-decenoic acid cyclohexyl ester, trans-2-decenoic acid isopropyl ester, and trans-9-decenoic acid methyl ester.

10. The method of claim 9, wherein the ester of the decenoic acid is trans-2-decenoic acid ethyl ester.

* * * * *